(12) United States Patent
Ogura

(10) Patent No.: US 7,453,573 B2
(45) Date of Patent: Nov. 18, 2008

(54) APPARATUS AND METHOD FOR MEASURING INTERACTION BETWEEN MEASUREMENT-TARGET SAMPLE SUBSTANCE AND BIOACTIVE SUBSTANCE

(75) Inventor: Nobuhiko Ogura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/905,029

(22) Filed: Sep. 27, 2007

(65) Prior Publication Data

US 2008/0079944 A1  Apr. 3, 2008

(30) Foreign Application Priority Data

Sep. 27, 2006  (JP) .............. 2006-262423

(51) Int. Cl.
  *G01J 1/00*  (2006.01)
  *G01N 21/01*  (2006.01)
  *B01L 3/00*  (2006.01)
(52) U.S. Cl. ............... 356/445; 356/440; 422/82.05; 422/99; 435/286.1; 435/287.1
(58) Field of Classification Search ............ 356/39–42, 356/440, 445–448, 246; 250/339.12, 340, 250/341.5; 422/82.05, 68.1, 67, 99; 435/286.1, 435/287.1; 436/95, 164
See application file for complete search history.

(56) References Cited

U.S. PATENT DOCUMENTS 4,731,154 A * 3/1988 Hausman Hazlitt et al. ... 216/85
5,376,254 A * 12/1994 Fisher .................. 204/403.01
6,471,136 B1 * 10/2002 Chatterjee et al. ........... 237/2 B
7,238,536 B1 * 7/2007 Schlenoff .................. 436/172
2004/0175811 A1 * 9/2004 Kling et al. ................. 435/174

FOREIGN PATENT DOCUMENTS

DE  102006014986 A1 * 10/2007
JP      2758904 B2    3/1998

OTHER PUBLICATIONS

Biacore, "Protocols for Measuring Low Molecular Weight Compounds", Application Training, pp. 6-9, 2001.

* cited by examiner

*Primary Examiner*—Sang Nguyen
(74) *Attorney, Agent, or Firm*—Sughrue Mion, PLLC

(57) ABSTRACT

A measuring apparatus and a measuring method are configured to measure a concentration of an organic solvent in a sample solution, measure a concentration of the organic solvent in a concentration control solution, calculate a mixture amount by which the concentration control solution is mixed into the sample solution of a preset amount so that the concentration of the organic solvent in the sample solution is equal to a preset concentration based on the two concentrations, mix the concentration control solution of the calculated mixture amount with the sample solution of the preset amount, supply a mixture solution obtained by the mixing unit to a measurement region in which a bioactive substance is immobilized in advance, and measure an interaction between the bioactive substance and the sample substance in the mixture solution based on a result of measuring a refraction index of a light incident on the measurement region.

12 Claims, 17 Drawing Sheets

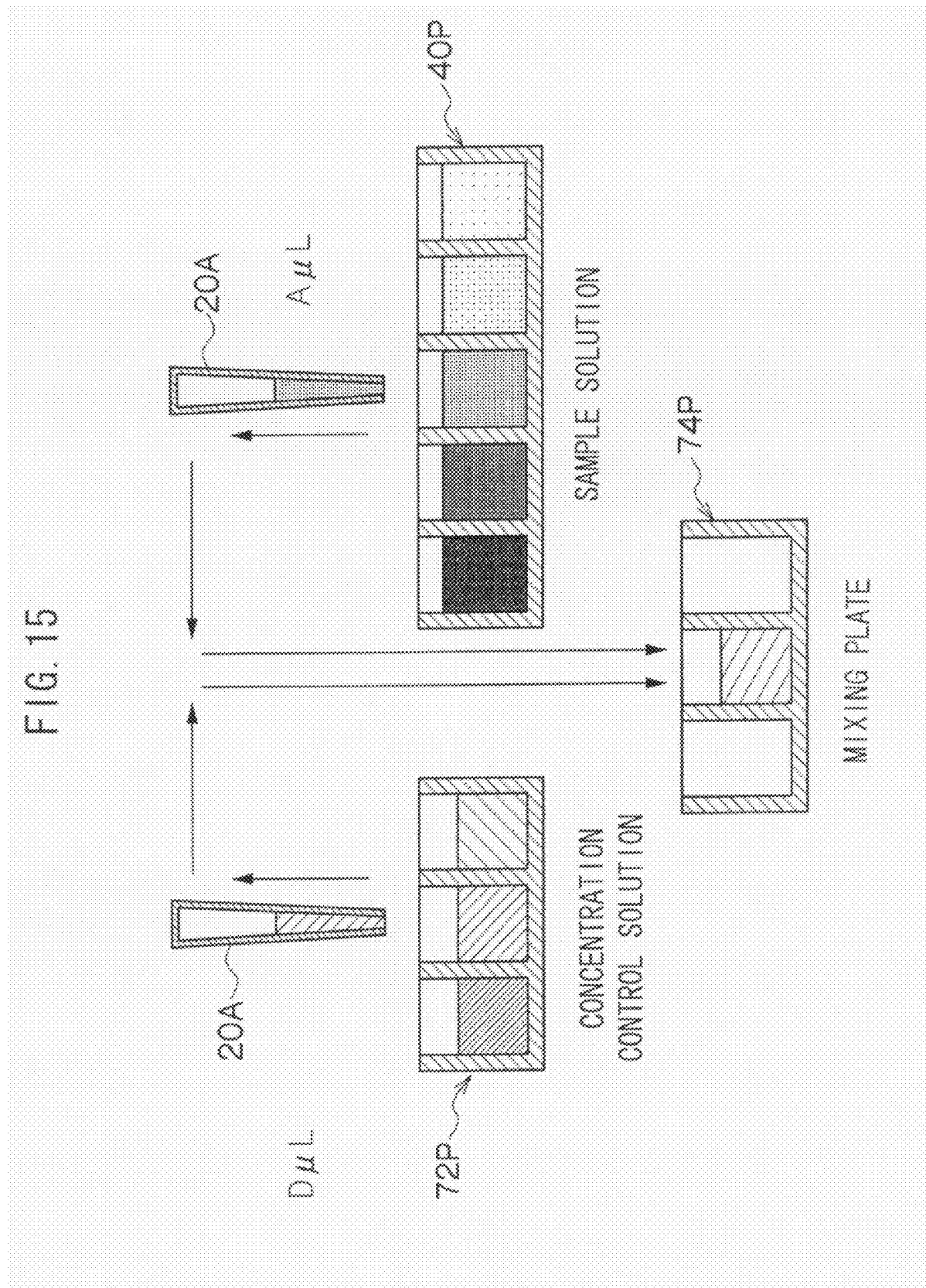

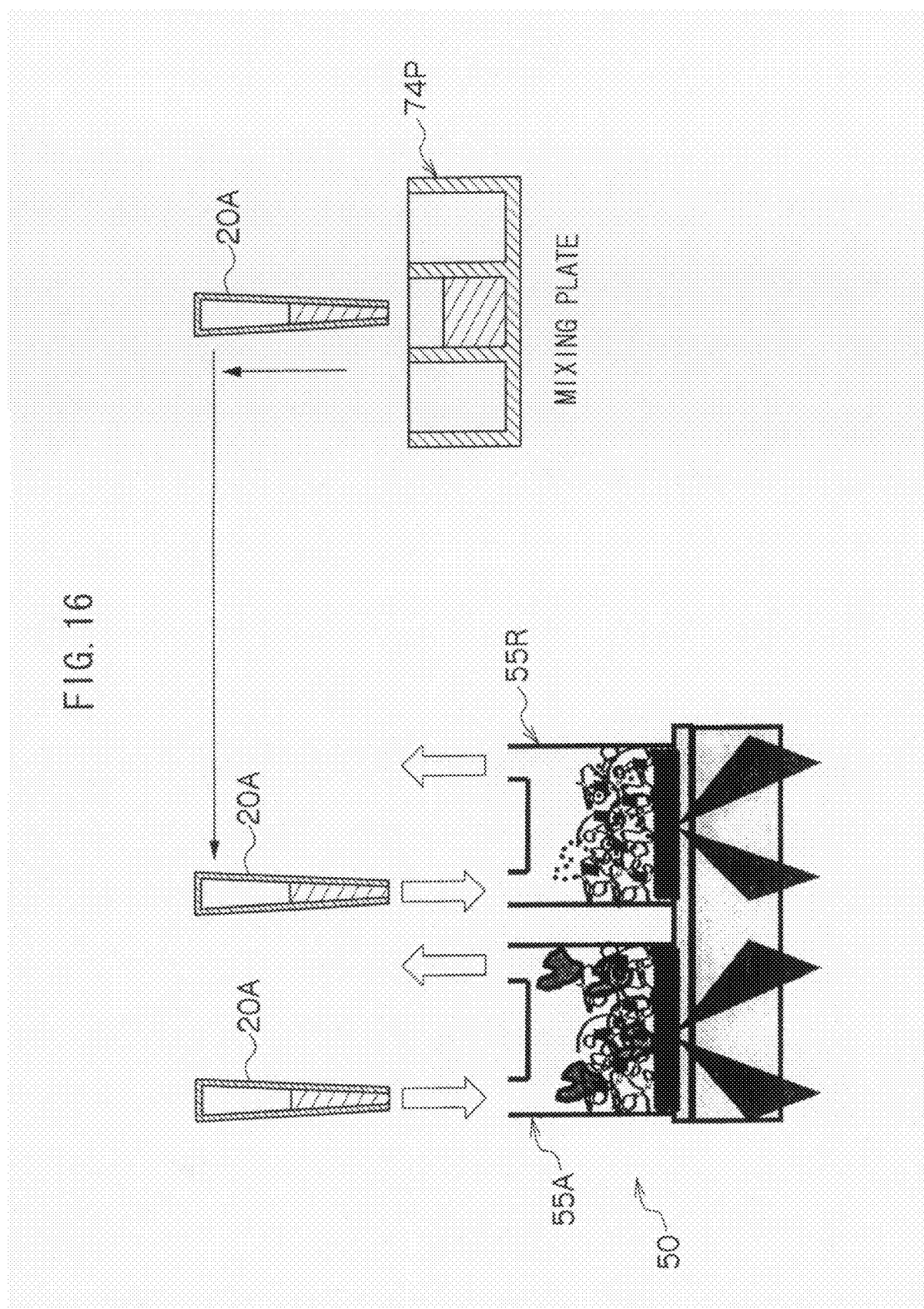

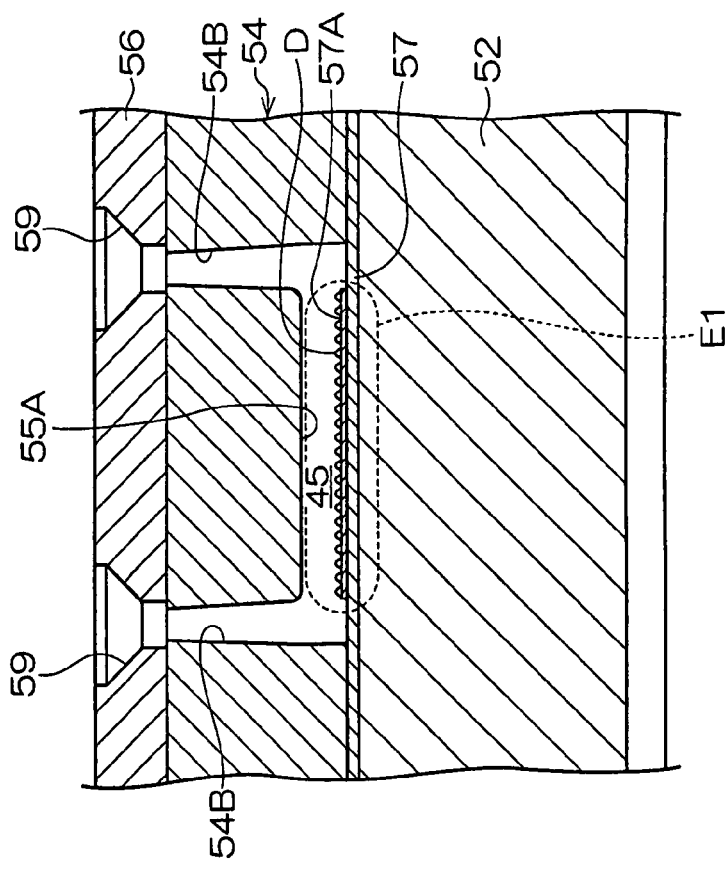
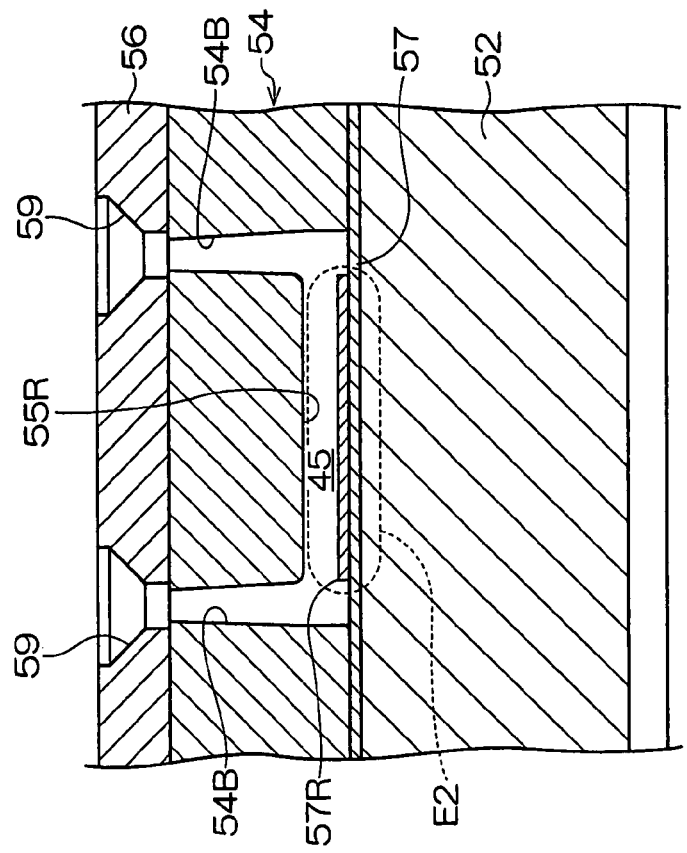

APPARATUS AND METHOD FOR MEASURING INTERACTION BETWEEN MEASUREMENT-TARGET SAMPLE SUBSTANCE AND BIOACTIVE SUBSTANCE

CROSS-REFERENCE TO RELATED APPLICATION

This application claims priority under 35 USC 119 from Japanese Patent Application No. 2006-262423, the disclosure of which is incorporated by reference herein.

BACKGROUND

1. Technical Field

The invention relates to a measuring apparatus and a measuring method for measuring an interaction between a measurement-target sample substance and a bioactive substance.

2. Related Art

Conventionally, a technique for selecting a sample substance containing functional groups bonded to reactive groups contained in a bioactive substance from among various candidates is known. Examples of the bioactive substance include specific proteins. The sample substance, such as a nucleic acid or a derivative thereof, combined with such a specific bioactive substance is expected to be used mainly in the field of medicine.

As a method of selecting a sample substance to be combined with a bioactive substance, various methods of evaluating an interaction between the bioactive substance and the sample substance have been used. An evaluation method using near field light because of no need of label and high sensitivity is known as an evaluation method. Examples of the method of measuring the interaction using the near field light include a method using surface plasmon resonance as disclosed in, for example, Japanese Patent (JP) No. 2758904 and Biacore Application Training.

Generally, if the interaction between the bioactive substance and the sample substance is to be measured using the surface plasmon resonance, then a sample solution obtained by dissolving the measurement-target sample substance into an organic solvent is supplied to a measurement region arranged on one surface of a prism and made of a bioactive substance-immobilized film, a laser beam is irradiated onto the bioactive substance-immobilized film at various angles so as to obtain a total reflection condition on an interface between the bioactive substance-immobilized film and the bioactive substance, and the interaction between the bioactive substance and the sample substance is measured based on a result of detecting a refraction index of the light totally reflecting on this interface.

Furthermore, to acquire more accurate information, the following method is sometimes employed. A measurement region in which a bioactive substance is immobilized and a reference region in which the bioactive substance is unimmobilized are provided. By correcting signal information acquired from the measurement region using signal information acquired from the reference region, the interaction between the sample substance and the bioactive substance is shown.

According to a technique disclosed in, for example, the Biacore Application Training, a plurality of kinds of concentration control solutions different in organic solvent concentration are prepared. Refraction indexes are measured when the concentration control solutions having different organic solvent concentrations are supplied to each of the reference region and the measurement region. The relationship between the refraction index measurement result and the organic solvent concentration in each of the reference region and the measurement region is obtained in advance. In an ideal state, the relationship between the refraction index measurement result and the organic solvent concentration is a primary linear relationship (hereinafter, referred to as "ideal linear line"). In the measurement region, the ideal line differs from the reference region in inclination because of immobilization of the bioactive substance onto the bioactive substance-immobilized film. Due to this, the refraction index measurement result in the measurement region and that in the reference region obtained by supplying the sample solutions to each of the measurement region and the reference region are corrected based on the organic solvent concentrations of the respective sample solutions and the primary linear relationship obtained in advance, thereby measuring the interaction between the bioactive substance and the sample substance.

However, the relationship between the organic solvent concentration and the refraction index measurement result is not actually the primary linear relationship but has a slight offset (so-called linearity error) with respect to the ideal line. Due to this, if the above-stated method is used, the measurement result indicating that there is actually an interaction between the bioactive substance and the sample substance although there is actually no interaction therebetween may possibly obtained. Furthermore, even if there is an interaction between the bioactive substance and the sample substance, the measurement results indicating a different amount from an actual interaction amount (e.g., a combined amount between the bioactive substance and the sample substance) are sometimes obtained.

To dissolve the sample substance, the above-stated organic solvent is used. It is known that the refraction index of the organic solvent is so high as to influence refraction index information that indicates the interaction between the bioactive substance and the sample substance. Due to this, a concentration fluctuation of the sample solution resulting from a fluctuation in the concentration of the organic solvent in the sample solution due to evaporation or the like is one cause for the linearity error.

SUMMARY

The invention has been achieved in view of the above-stated situations. It is an object of the invention to provide a measuring apparatus and a measuring method capable of suppressing deterioration in measurement accuracy during measurement of an interaction between a bioactive substance and a sample substance.

According to a first aspect of the invention, there is provided a measuring apparatus comprising: a first measuring unit for measuring a concentration of an organic solvent in a sample solution obtained by dissolving a sample substance as a measurement target in the organic solvent; a second measuring unit for measuring a concentration of the organic solvent in a concentration control solution which does not contain the sample substance but contains the organic solvent; a calculating unit for calculating a mixture amount of the concentration control solution to be mixed into a preset amount of the sample solution so that the concentration of the organic solvent in the sample solution is equal to a preset concentration based on the concentration measured by the first measuring unit and the concentration measured by the second measuring unit; a mixing unit for mixing the mixture amount of the concentration control solution calculated by the calculating unit with the preset amount of the sample solution; and a third measuring unit for supplying a mixture solution obtained by the mixing unit to a measurement region in which a bioactive substance is immobilized in advance, and measuring an interaction between the bioactive substance and the sample substance in the mixture solution based on a result of measuring a refraction index of a light incident on the measurement region.

According to a second aspect of the invention, there is provided a measuring method comprising: a first measuring process of measuring a concentration of an organic solvent in a sample solution obtained by dissolving a sample substance as a measurement target in the organic solvent; a second measuring process of measuring a concentration of the organic solvent in a concentration control solution which does not contain the sample substance but contains the organic solvent; calculating a mixture amount of the concentration control solution to be mixed into a preset amount of the sample solution so that the concentration of the organic solvent in the sample solution becomes equal to a preset concentration based on the concentration measured by the first measuring process and the concentration measured by the second measuring process; mixing the mixture amount of the concentration control solution calculated in the calculating with the preset amount of the sample solution; and a third measuring process of supplying a mixture solution obtained by the mixing to a measurement region in which a bioactive substance is immobilized in advance, performing an analysis using a refraction index of a light incident on the measurement region, and measuring an interaction between the bioactive substance and the sample substance in the mixture solution.

Other aspects, features and advantages of the present invention will become apparent from the following description taken in conjunction with the accompanying drawings.

BRIEF DESCRIPTION OF THE DRAWINGS

FIG. 15 is a pattern diagram showing a step of supplying the concentration control solution extracted from the concentration control solution plate and the sample solution extracted from the sample solution plate to a mixing plate, and regulating a mixture solution according to an embodiment of the invention.

FIG. 16 is a pattern diagram showing a step of supplying the mixture solution extracted from the mixing plate to the measurement region (measurement channel) and the reference region (reference channel) according to an embodiment of the invention;

FIG. 17A is a cross-sectional view of a reference channel part of the measuring stick according to an embodiment of the invention.

FIG. 17B is a cross-sectional view of a measurement channel part of the measuring stick according to an embodiment of the invention.

DETAILED DESCRIPTION

Figure 1:
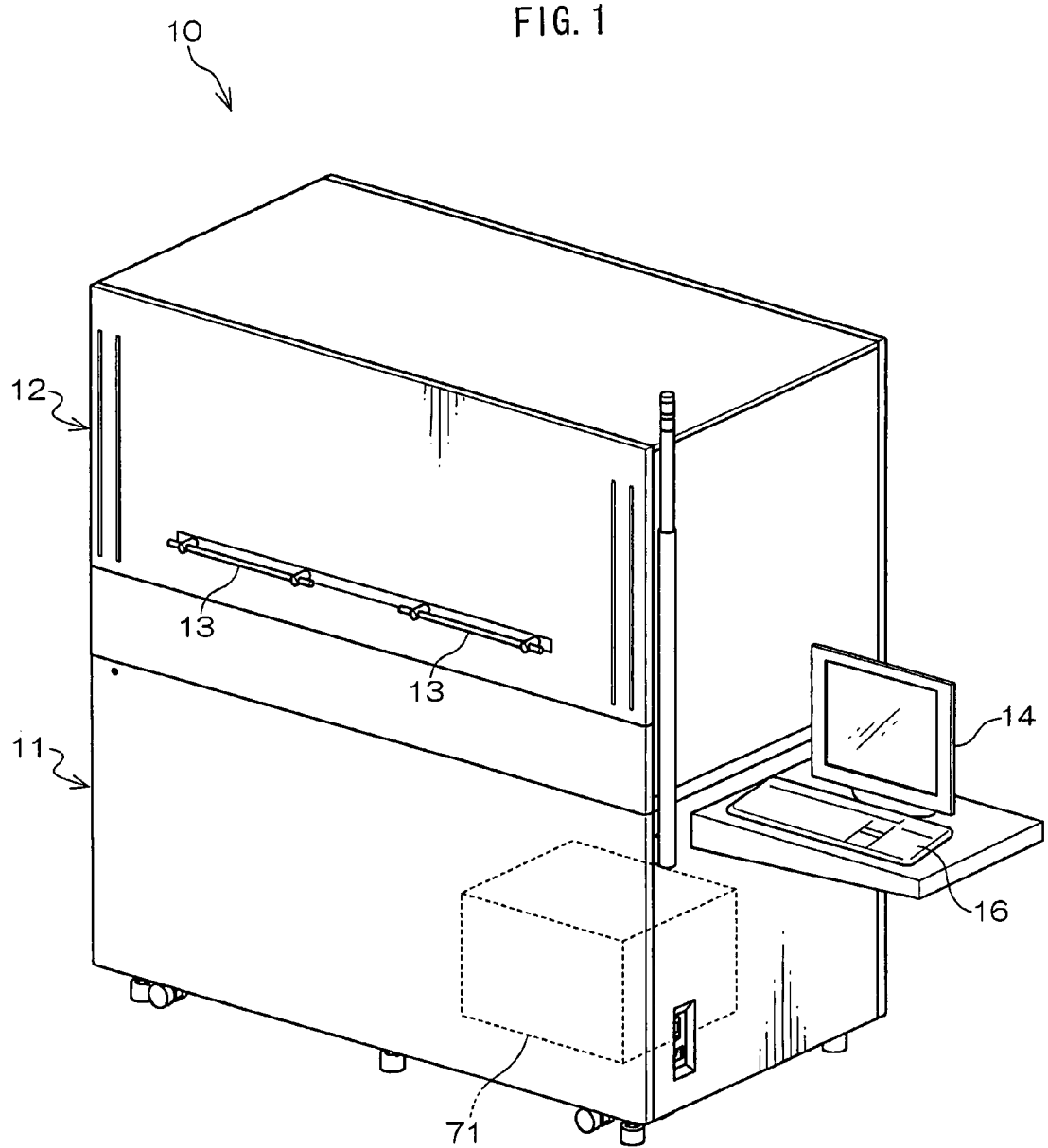
FIG. 1 is a perspective view of a biosensor according to an embodiment of the invention.

An exemplary embodiment of a measuring apparatus and a measuring method according to the invention will be described hereinafter in detail with reference to the accompanying drawings.

As shown in FIGS. 1 to 4, a biosensor 10 according to the embodiment includes a lower housing 11 and an upper housing 12. The upper housing 12 is made of a heat insulating member and entirely covers an upper half of the biosensor 10. An interior of the upper housing 12, an exterior of the upper housing 12, and an interior of the lower housing 11 are heat-insulated from one another. A front side of the upper housing 12 is openable upward, and a grip 13 is attached to the front side thereof. A display unit 14 and an input unit 16 are arranged outside of the upper housing 12.

Examples of the display unit 14 include display devices such as a CRT and an LCD. Examples of the input unit 16 include a touch panel and a keyboard.

A main controller 71 connected to the display unit 14 and the input unit 16 so as to be able to transmit and receive signals to and from the display unit 14 and the input unit 16 and controlling respective constituent elements provided in the biosensor 10 is provided inside of the upper housing 12.

Figure 2:
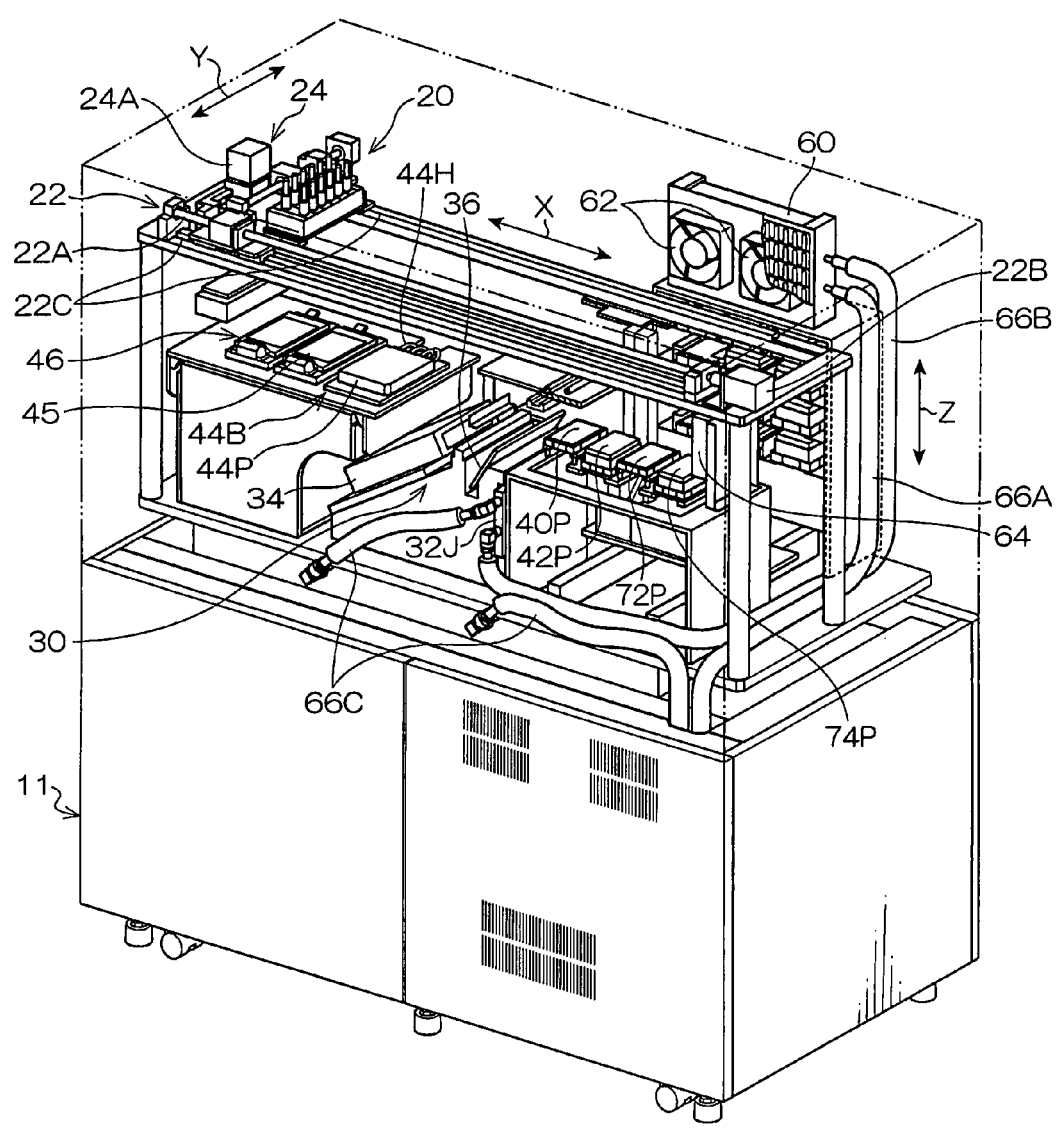
FIG. 2 is a perspective view of an interior of the biosensor according to an embodiment of the invention.
Figure 3:
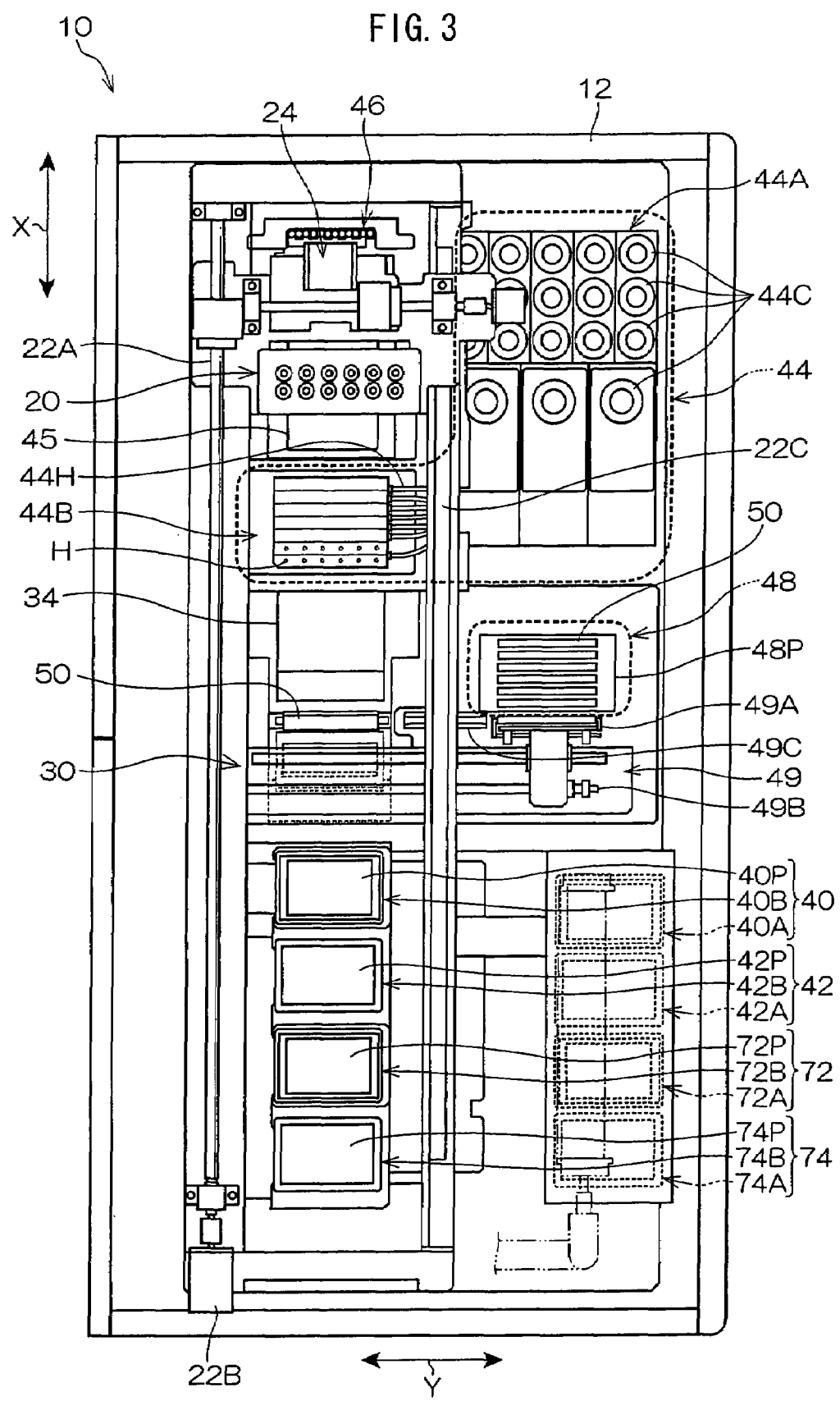
FIG. 3 is a top view of the interior of the biosensor according to an embodiment of the invention.
Figure 4:
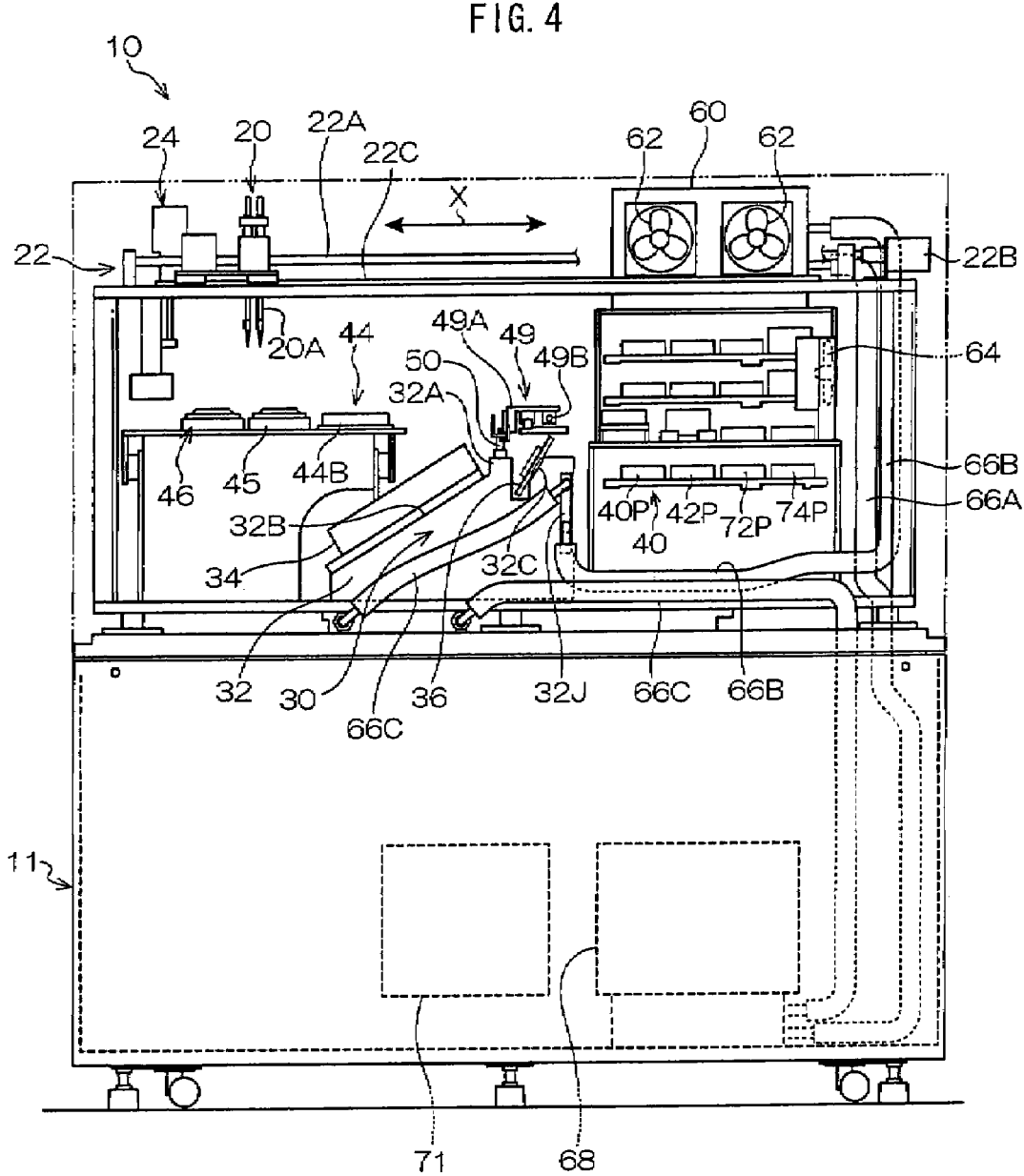
FIG. 4 is a side view of the interior of the biosensor according to an embodiment of the invention.

FIG. 2 is a perspective view showing an interior of the biosensor 10 from a back side of FIG. 1 with the upper housing 12 removed. FIG. 3 is a top view showing an interior of the upper housing 12 from above. FIG. 4 is a side view of the interior of the biosensor 10 from a front side of FIG. 2.

The upper housing 12 includes therein a dispensing head 20, a measuring unit 30, a sample solution stocking unit 40, a pipette tip stocking unit 42, a buffer solution stocking unit 44, a cold insulating unit 46, a measuring tip stocking unit 48, a concentration control solution stocking unit 72, a mixing unit 74, a radiator 60, a radiator blower fan 62, and a horizontal blower fan 64.

The sample solution stocking unit 40 is configured to include a sample solution stack unit 40A and a sample solution setting unit 40B. A plurality of sample solution plates 40P are stacked in a Z direction and contained in the sample solution stack unit 40A.

Each of the sample solution plates 40P is configured to include a plurality of cells (not shown) for storing therein a sample solution containing a sample substance. Each cell stores therein in advance the sample solution obtained by dissolving one or two or more different sample substances into an organic solvent.

One of the plural sample solution plates 40P stacked in the sample solution stack unit 40A is transported from the sample solution stack unit 40A to the sample solution setting unit 40B by a transport mechanism (not shown) and set to the sample solution setting unit 40B.

The sample substance is a measurement target substance to be measured by the biosensor 10 and is, for example, a nucleic acid molecule. Examples of the nucleic acid molecule include a nucleic acid and a nucleic acid derivative, i.e., include DNA, RNA, and derivatives of the DNA and RNA, i.e., matters obtained by partially alternating the DNA or RNA present in nature. Examples of the nucleic acid derivative include a PNA (peptide nucleic acid) that is a compound having a structure similar to the DNA and forming a skeleton by peptide bond.

Each of the cells of each sample solution plate 40P stores therein in advance the sample solution obtained by dissolving this sample solution into the solvent.

As the solvent for dissolving the sample substance, an organic solvent is used. The organic solvent is preferably one having no influence on the sample substance such as an organic substance that does not cause alternation of the sample substance itself. Specifically, at least one selected from a group consisting of dimethyl sulfoxide (DMSO), N-methylformamide, N-methylacetamide, N,N-dimethylformamide (DMF), N,N-dimethylacetamide, N-methyl-2-pyrrolidone, and γ-butyl lactone can be used as the organic solvent. It is preferable to use DMSO among these organic solvents because DMSO is suitable as a storage solvent due to high water-miscibility, high dissolubility with respect to hydrophobic compounds, and low reactivity.

The pipette tip stocking unit 42 is configured to include a pipette tip stack unit 42A and a pipette tip setting unit 42B. A plurality of pipette tip stocking units 42P for holding a plurality of pipette tips is stacked in the Z direction (vertical direction) and contained in the pipette tip stack unit 42A. One of the pipette tip stocking units 42P is transported from the pipette tip stack unit 42A to the pipette tip setting unit 42B by a transport mechanism (not shown) and set to the pipette tip setting unit 42B.

The buffer solution stocking unit 44 is configured to include a bottle container 44A and a buffer solution supply unit 44B. A plurality of bottles 44C having a buffer solution stored therein are contained in the bottle container 44A.

As the buffer solution, a solution which basically contains a well-known buffer solution (see "Chemical Handbook, Applied Chemistry $2^{nd}$ edition", pp. 1312 to 1320) and to which salt, a surfactant (e.g., Tween20), metal ions (e.g., magnesium ions, potassium ions, and calcium ions), a stabilizing agent (e.g., DTT) and the like are added can be used. Particularly, a PBS buffer solution (phosphate buffered saline), a Tris buffer solution, a HEPES buffer solution or the like is preferably used as the buffer solution.

A buffer solution plate 44P is set to the buffer solution supply unit 44B. The buffer solution plate 44P is divided into a plurality of compartments that store therein buffer solutions having different concentrations, respectively. Holes H into which the pipette tips CP are inserted at the time of access of the dispensing head 20 are formed in an upper portion of the buffer solution plate 44P. The buffer solutions are supplied to the buffer solution plate 44P from the bottles 44C by hoses 44H, respectively.

A correction plate 45 is arranged next to the buffer solution supply unit 44B, and the cold insulating unit 46 is arranged next to the correction plate 45. The correction plate 45 is a plate for adjusting the concentrations of the respective buffer solutions and configured to include a plurality of cells in a matrix. A sample solution necessary to keep cold is arranged in the cold insulating unit 46. The cold insulating unit 46 is kept to low temperature and the sample solution is kept in a low temperature state on the cold insulating unit 46.

The concentration control solution stocking unit 72 is configured to include a concentration control solution plate stacking unit 72A and a concentration control solution setting unit 72B. A plurality of concentration control solution plates 72P are stacked in the concentration control solution plate stacking unit 72A in the Z direction.

Each of the concentration control solution plates 72P is configured to include a plurality of cells (not shown) for storing therein a concentration control solution containing the organic solvent. The cells store therein in advance a plurality of types of concentration control solutions containing organic solvents having different concentrations, respectively.

Each of the concentration control solutions is a solution containing the organic solvent and the buffer solution for controlling the concentration of the organic solvent in the sample solution as will be described later in detail.

Although it is basically preferable that the organic solvent in the concentration control solution is the same in type as that in the sample solution, they may be different.

As for the concentration of the organic solvent contained in the concentration control solution, a plurality of types of concentration control solutions containing the organic solvents having different concentration are stored in a plurality of cells of the concentration control solution plates 72P to correspond to the cells in preset regions, respectively so as to be able to control the concentration of the organic solvent in the measurement-target sample solution in advance.

One of the plural concentration control solution plates 72P stacked in the concentration control solution plate stacking unit 72A is transported from the concentration control solution stack unit 72 to the concentration control solution plate setting unit 72B by a transport mechanism (not shown) and set to the concentration control solution plate setting unit 72B.

The mixing unit 74 is configured to include a mixing plate stacking unit 74A and a mixing plate setting unit 74B. A plurality of mixing plates 74P are stacked in the mixing plate stacking unit 74A in the Z direction. One of the mixing plates 74P is transported from the mixing plate stacking unit 74A to the mixing plate setting unit 74B by a transport mechanism (not shown) and set to the mixing plate setting unit 74B.

Each of the mixing plates 74P is configured to include a plurality of cells (not shown). Each of the cells is a concave portion for adjusting a mixture solution that is a mixture of the concentration control solution and the sample solution. The cells are provided to correspond to a plurality of fluid channels 55 for measurement sticks 50, respectively. Each of the fluid channels 55 is a pair of a measurement channel 55A and a reference channel 55R to be described later in detail.

A measurement tip storage plate 48P is set to the measurement tip stocking unit 48. A plurality of measurement sticks 50 serving as measurement tips are stored in the measurement tip storage plate 48P.

A measurement tip transport mechanism 49 is arranged between the measurement tip stocking unit 48 and the measuring unit 30. The measurement tip transport mechanism 49 is configured to include a holding arm 49A holding and putting the measurement stick 50 between both sides, a ball spring 49B moving the holding arm 49A in a Y direction by rotating the holding arm 49A, and a transport rail 49C which is arranged in the Y direction and on which the measurement stick 50 is mounted. The measurement tip transport mechanism 49 is connected to a driving unit 49D (see FIG. 11) such as a motor for driving the respective constituent elements of the measurement tip transport mechanism 49 so as to be able to transmit and receive signals to and from the driving unit 49D. The driving unit 49D is connected to the main controller 71 so as to be able to transmit and receive signals to and from the main controller 71 and driven under control of the main controller 71. During measurement, one measurement stick 50 is transported from the measurement tip storage plate 49P to the transport rail 49C by the measurement tip transport mechanism 49 and mounted on the transport rail 49C, moved to the measuring unit 30 while being held between the both sides of the holding arm 49A, and set to the measuring unit 30.

Figure 5:
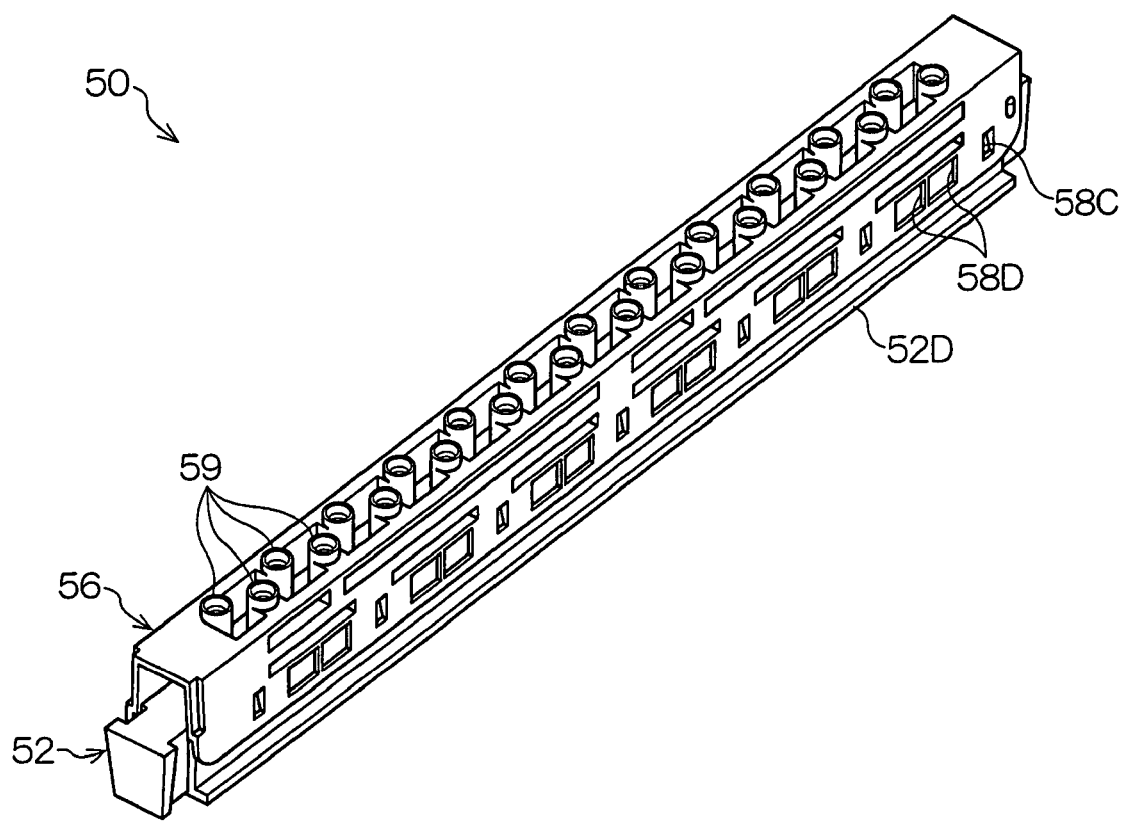
FIG. 5 is a perspective view of a measuring stick according to an embodiment of the invention.
Figure 6:
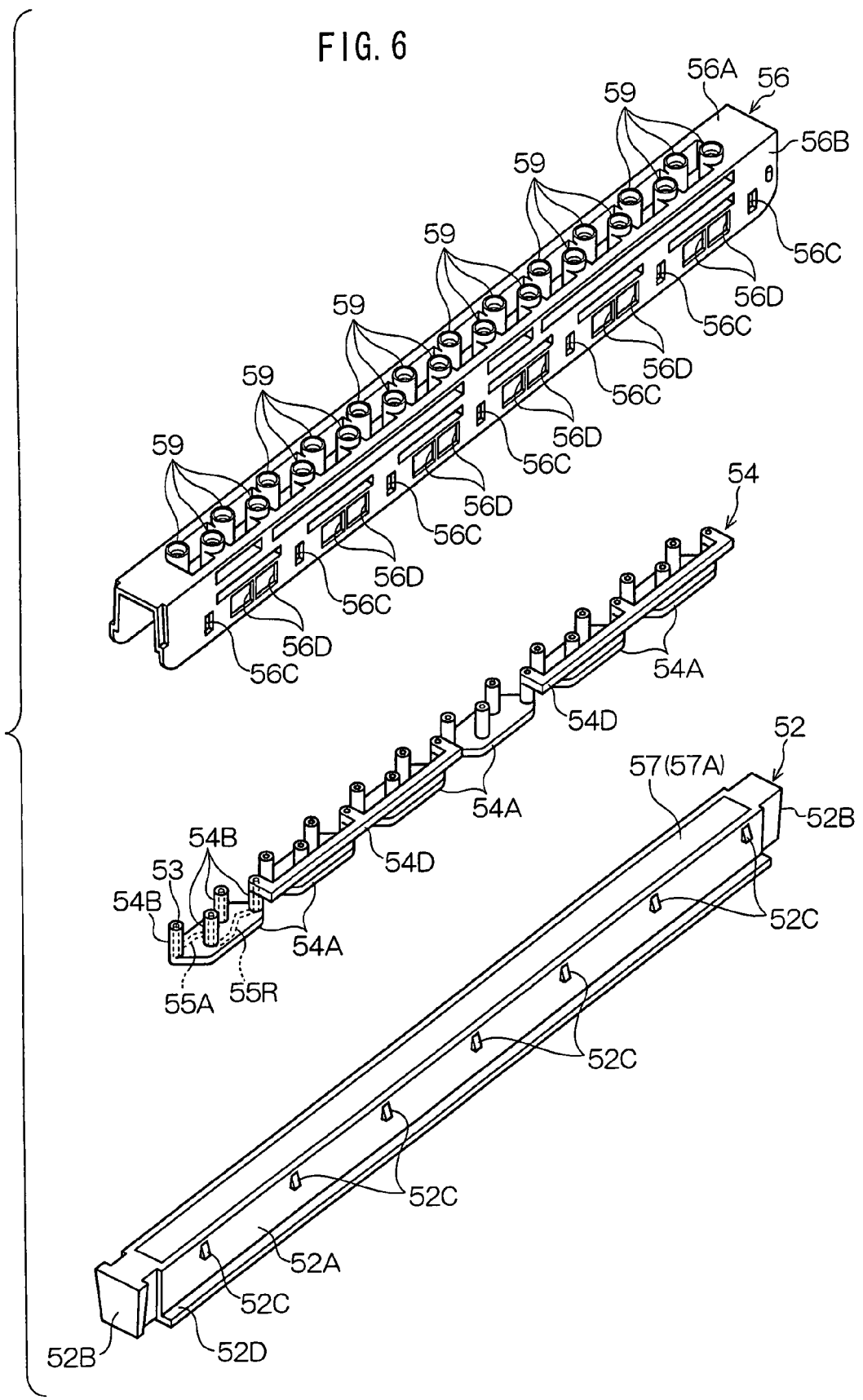
FIG. 6 is an exploded perspective view of the measuring stick according to an embodiment of the invention.

As shown in FIGS. 5 and 6, each of the measurement sticks 50 is configured to include a dielectric block 52, a channel member 54, and a holding member 56.

The dielectric block 52 is made of a transport resin or the like transmitting an irradiated light, and includes a prism unit 52A having a trapezoidal rod-shaped cross section and held units 52B formed integrally with the prism unit 52A and arranged on both ends of the prism unit 52A, respectively. A metal film 57 is formed on an upper surface on the wider side of two surfaces of the prism unit 52A parallel to each other. The dielectric block 52 acts as a so-called prism. When the biosensor 10 makes a measurement, an irradiation light is incident on the dielectric block 52 from one of two side surfaces of the prism unit 52A opposed and not parallel to each other, and the irradiation light totally reflected by an interface between the metal film 57 and the dielectric block 52 is emitted from the other side surface thereof.

Engagement convex portions 52C engaged with the holding member 56 are formed along an upper side edge on both side surfaces of the prism unit 52A. A flange unit 52D engaged with the transport rail 49C is formed along a lower side edge of the prism unit 52A.

As shown in FIG. 6, the channel member 54 includes six base units 54A and four cylindrical members 54B are built on each of the base units 54A. An upper portion of one of the cylindrical members 54B of each of the base units 54A is coupled to one another by a coupling member at intervals of three base units 54A. The channel member 54 can be constituted by a soft and elastically deformable material, e.g., amorphous polyolefin elastomer. By thus constituting the channel member 54 by the elastically deformable material, it is possible to enhance adhesiveness of the channel member 54 to the dielectric block 52 and to ensure closeness of the fluid channel 55 constituted between the channel member 54 and the dielectric member 52.

Figure 7:
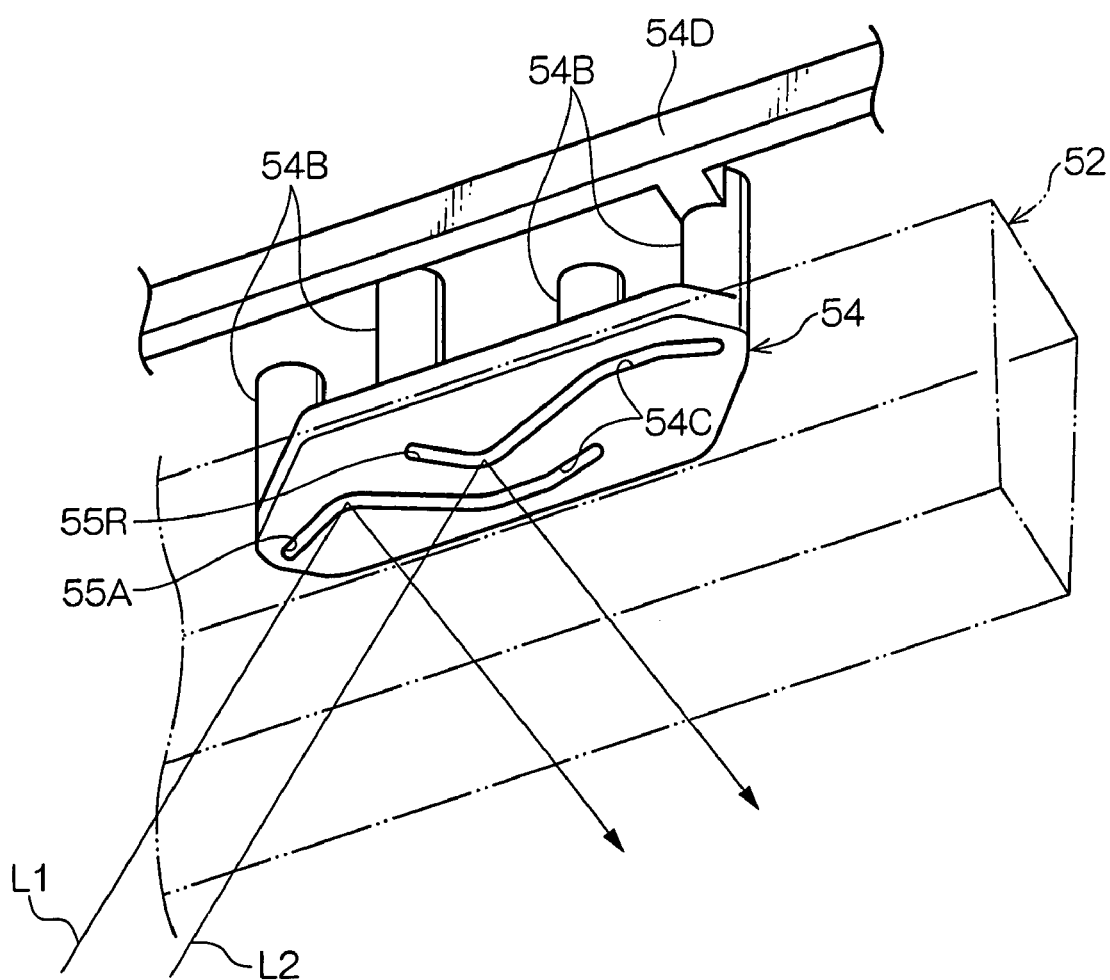
FIG. 7 is a pattern diagram showing a state in which an irradiation light is incident on a measurement region and a reference region of the measuring stick according to an embodiment of the invention.

As shown in FIGS. 6 and 7, two generally S-shaped channel grooves 54C are formed on a bottom of each of the base units 54A. Each of ends of the channel grooves 54C is communicated with a hollow portion of one cylindrical member 54B.

A bottom of each base unit 54A is closely attached to a measurement surface (an upper surface) of the dielectric block 52, whereby a fluid channel 55 is constituted by a space formed between the channel grooves 54C and the upper surface of the dielectric block 52 and the hollow portion. Two fluid channels 55 are constituted on one base unit 54A. In each of the fluid channels 55, two ports 53 of the fluid channel 55 are formed on an upper end surface of the cylindrical member 54B.

Out of the two fluid channels 55, one is used as a measurement channel 55A and the other as a reference channel 55R. As shown in FIG. 17B, the measurement channel 55A is a channel including a measurement region E1 in which a bioactive substance is immobilized. As shown in FIG. 17A, the reference channel 55R is a channel including a measurement region E2 in which the bioactive substance is not immobilized.

More specifically, as shown in FIG. 17B, a linker layer 57A to the surface of which the bioactive substance is immobilized in advance is formed on a surface of the metal film 57 located in the measurement channel 55A. The linker layer 57A is a layer for immobilizing the bioactive substance onto the metal film 57. By producing covalent bond in the bioactive substance via functional groups of the linker layer 57A, the bioactive substance is immobilized onto the metal film 57.

The bioactive substance is a substance interacting with the measurement target sample substance. The bioactive substance is not limited to a specific substance as long as the bioactive substance interacts with the measurement target sample substance. Examples of the bioactive substance include immune proteins, enzymes, microorganisms, nucleic acids, low-molecular-weight organic compounds, nonimmune proteins, immunoglobulin-binding proteins, sugar-binding proteins, sugar-recognizing sugar chain, fatty acids or fatty acid esters, polypeptides or oligopeptides each having ligand-binding ability.

If the sample substance is supplied onto the bioactive substance and the supplied sample substance includes functional groups reacting with reactive groups of the bioactive substance, interaction (that is, bond) occurs between the bioactive substance and the sample substance. Due to this, by supplying the sample solution to the bioactive substance and contacting the sample solution with the bioactive substance, it is possible to detect the sample substance interacting with the bioactive substance or measure the interaction between them. Thus, the measurement region E1 functions as a region for measuring the interaction between the sample substance and the bioactive substance D.

Furthermore, as shown in FIG. 17A, a linker layer 57R to the surface of which the bioactive substance is not immobilized is formed on the surface of the metal film 57 located in the reference channel 55R. The linker layer 57R is a layer to the surface of which the bioactive substance is not immobilized and on which the interaction between the bioactive substance and the sample substance cannot occur, differently from the linker layer 57A formed in the measurement channel 55A. The reference region E2 is a region provided to correct the measurement result in the measurement region E1.

Figure 8:
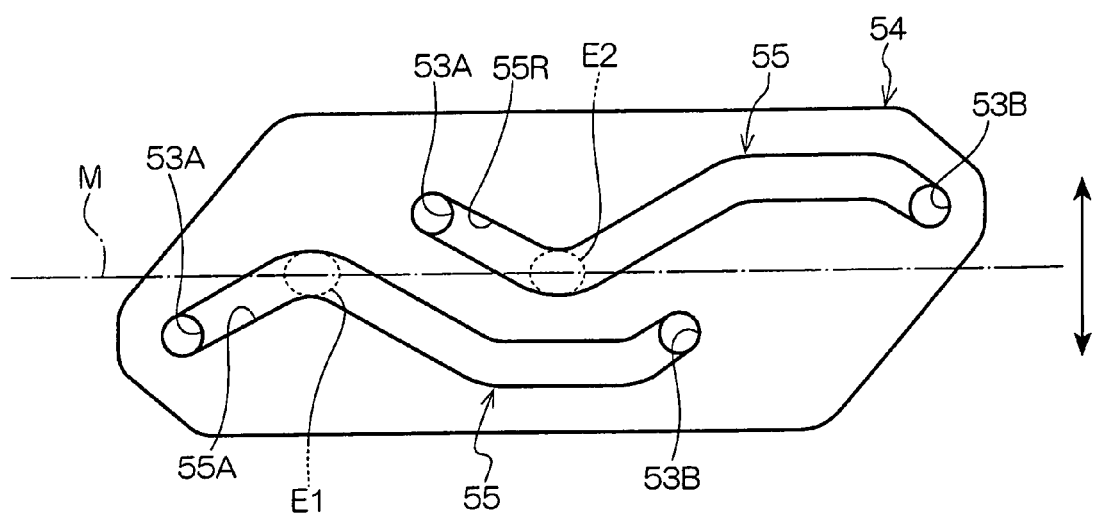
FIG. 8 is a schematic diagram showing one channel member of the measuring stick according to an embodiment of the invention when viewed from below.

As shown in FIG. 7, irradiation lights L1 and L2 are incident on the measurement channel 55A and the reference channel 55R, respectively. As shown in FIG. 8, the irradiation lights L1 and L2 are irradiated on S-shaped bent portions arranged on a center line M of the base unit 54A, respectively. Namely, an irradiation region of the irradiation light L1 in the measurement region 55A corresponds to the measurement region E1 whereas an irradiation region of the irradiation light L2 in the measurement region 55R corresponds to the measurement region E2.

The holding member 56 of the measurement stick 50 is long and configured so that an upper member 56A and two side plates 56B are formed into a box shape. Engagement holes 56C engaged with the respective engagement concave portions 52C of the dielectric block 52 are formed in each of the side plates 56B, and windows 56D are formed in portions of each side plate 56B corresponding to optical paths of the respective irradiation lights L1 and L2. The holding member 56 is attached to the dielectric block 52 by engaging the engagement holes 56C with the respective engagement concave portions 52C. The channel member 54 is formed integrally with the holding member 56 and arranged between the holding member 56 and the dielectric block 52.

Receiving units 59 are formed on the upper member 56A at positions corresponding to the respective cylindrical members 54B of the channel member 54. The receiving units 59 are generally cylindrical. As shown in FIG. 17, the receiving units 59 are preferably tapered toward the channel member 54.

As shown in FIG. 2, the dispensing head 20 is provided in an upper portion in the upper housing 12 and movable in an X direction by a horizontal driving mechanism 22. The horizontal driving mechanism 22 is configured to include a ball spring 22A, a motor 22B, and guide rails 22C. The ball spring 22A and the guide rails 22C are arranged in the X direction. Two guide rails 22C are arranged in parallel one of which is arranged below the ball spring 22A at a predetermined distance from the ball spring 22A. The dispensing head 20 is moved in the X direction along the guide rails 22C by rotation of the ball spring 22A.

Figure 9:
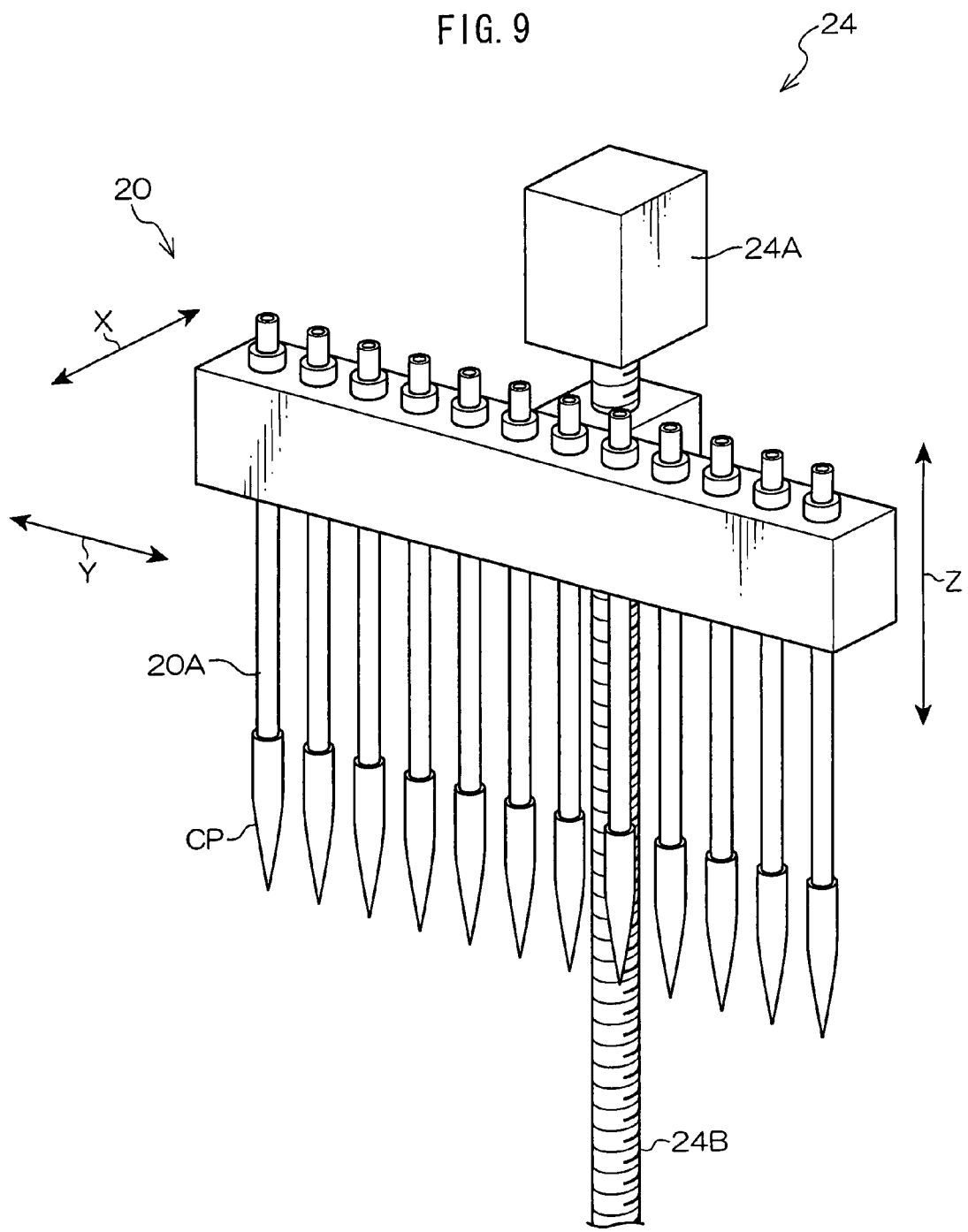
FIG. 9 is a perspective view of a vertical driving mechanism of a dispensing head of the biosensor according to an embodiment of the invention.

A vertical driving mechanism 24 for moving the dispensing head 20 in the Z direction is provided for the dispensing head 20. As shown in FIG. 9, the vertical driving mechanism 24 is configured to include a motor 24A and a driving shaft 24B arranged in the Z direction. The vertical driving mechanism 24 moves the dispensing head 20 in the Z direction.

The cold insulating unit 46, the correction plate 45, the buffer solution supply unit 44B (buffer solution plate 44P), the measuring unit 30 (measuring stick 50), the sample solution setting unit 40B (sample solution plate 40P), the pipette tip setting unit 42B (pipette tip stocking unit 42P), the concentration control solution setting unit 72B (concentration control solution plate 72P), and the mixture plate setting unit 74B (mixture plate 74P) to be accessed by the dispensing head 20 are arranged in the X direction (i.e., the moving direction of the dispensing head 20) in this order.

As shown in FIG. 9, the dispensing head 20 includes 12 dispensing tubes 20A. The dispensing tubes 20A are aligned in a Y direction orthogonal to the X direction. Pipette tips CP are attached to tip ends of the respective dispensing tubes 20A. The pipette tips CP are stored in the pipette tip stocking unit 42P and replaceable if it is necessary to do so.

When the biosensor 10 makes a measurement, the sample solution and the buffer solution are supplied from the dispensing tubes 20A to the measurement sticks 50. Two adjacent dispensing tubes 20A are paired and used to correspond to the ports of one fluid channel 55, respectively. Such solutions as the sample solution, the buffer solution, the concentration control solution, and the mixture solution (to be described later) are supplied to the measurement sticks 50 as follows. The dispensing head 20 is moved onto each of the cold insulating unit 46, the sample solution setting unit 40B, the concentration control solution setting unit 72B, and the mixture plate setting unit 74B, and each fluid is absorbed by the pipette tip CP attached to one of the paired adjacent dispensing tubes 20A (six in all).

If the absorbed fluid is to be supplied to the plural fluid channels 55 of the measurement sticks 50, an absorption amount of the fluid supplied to the fluid channels 55 is such an amount as to be able to supply the fluid to the two fluid channels 55, i.e., one measurement channel 55A and one reference channel 55R. The pipette tip CP of each of the six dispensing tubes 20A that absorbs the fluid is inserted into one port 53 (hereinafter, "supply port 53A") of the measurement channel 55A of the measurement stick 50 whereas the pipette tip CP of each of the six other dispensing tubes 20A is inserted into the other port 53 (hereinafter, referred to as "discharge port 53B") of the measurement channel 55A. A half amount of the fluid is discharged from the dispensing tubes 20A on the supply port 53A side, and the fluid is absorbed by the dispensing tubes 20A on the discharge port 53B side. Likewise, a remaining half amount of the fluid is supplied to the reference channel 55R side.

Figure 10:
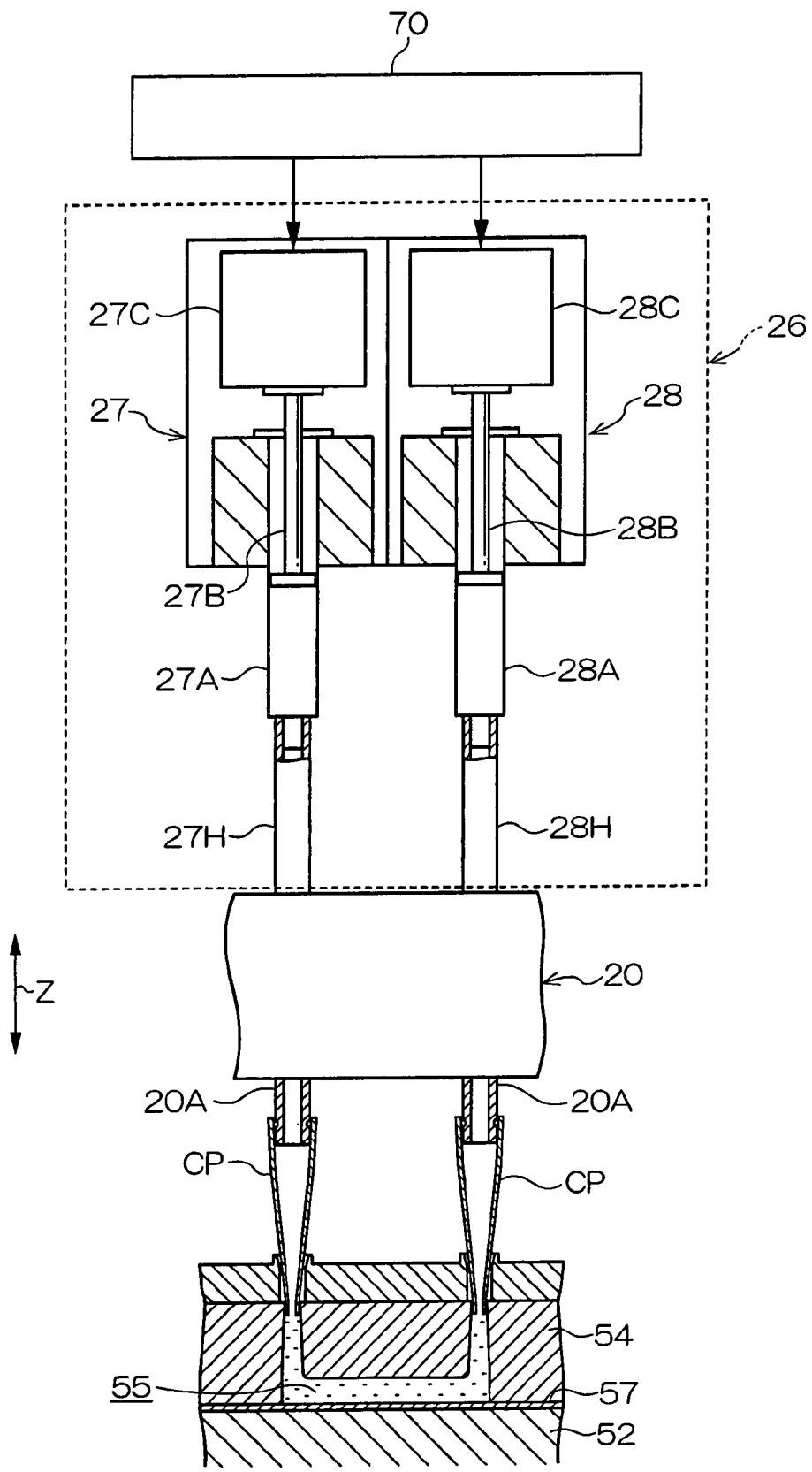
FIG. 10 is a schematic diagram showing a configuration of a liquid absorbing/discharging unit of the biosensor according to an embodiment of the invention.

As shown in FIG. 10, an absorption/discharge[intake and exhaust?] driving unit 26 is connected to each pair of adjacent dispensing tubes 20A. The absorption/discharge driving unit 26 includes a first pump 27 and a second pump 28. The first pump 27 and the second pump 28 are provided to correspond to the paired dispensing tubes 20A, respectively. The first pump 27 is a syringe pump and includes a first cylinder 27A, a first piston 27B, and a first motor 27C driving the first piston 27B. The first cylinder 27A is connected to the dispensing head 20 via a piping 27H. Likewise, the second pump 28 is a syringe pump and includes a second cylinder 28A, a second piston 28B, and a second motor 28C driving the second piston 28B. The second cylinder 28A is connected to the dispensing head 20 via a piping 28H. The first motor 27C and the second motor 28C are connected to the control unit 70 to be described later so as to be able to transmit and receive signals to and from the control unit 70.

Figure 11:
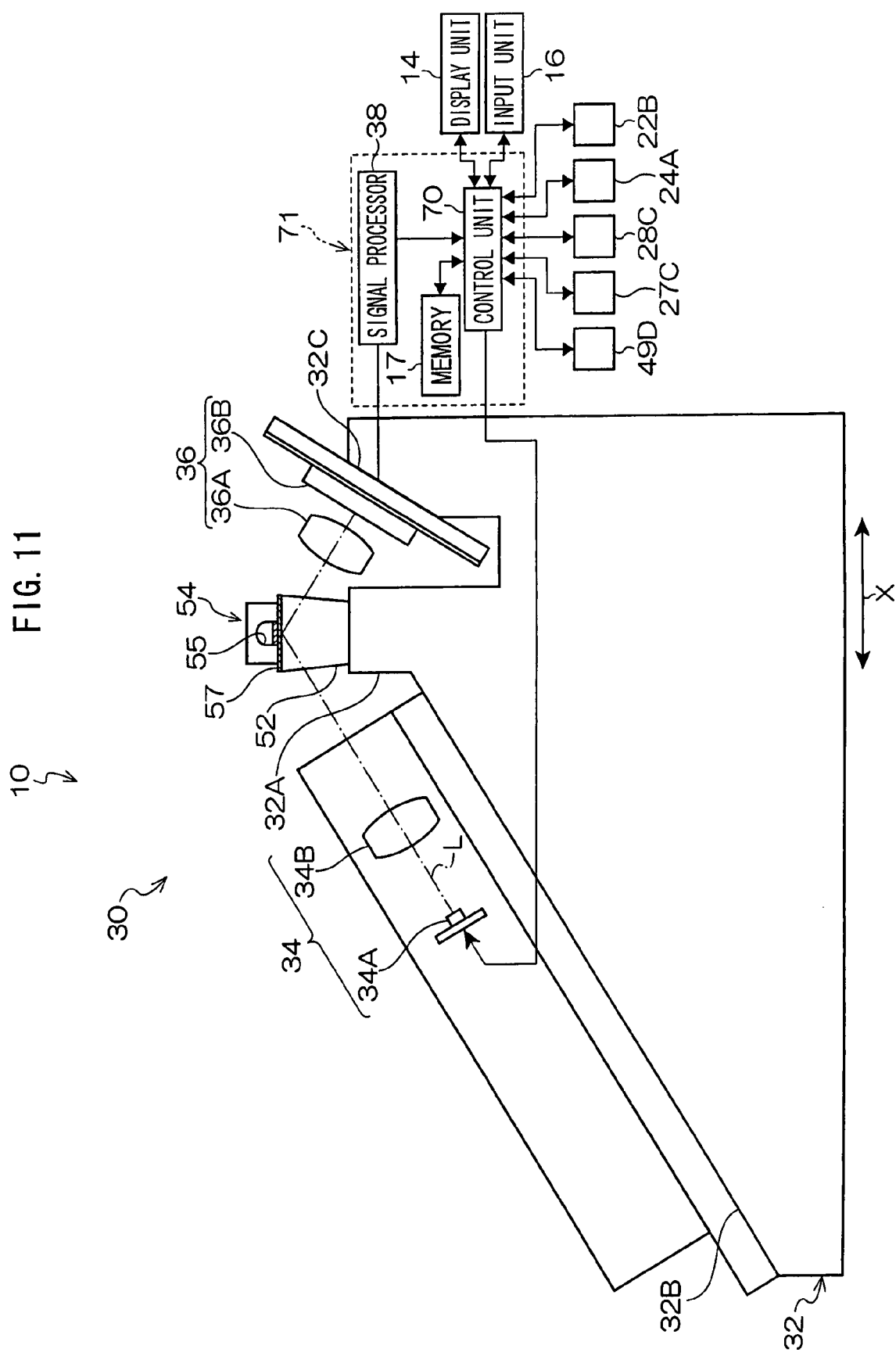
FIG. 11 is a schematic diagram showing a configuration of neighborhoods of an optical measuring unit of the biosensor and an electric configuration of the biosensor according to an embodiment of the invention.

As shown in FIG. 11, the biosensor 10 is configured to include the measuring unit 30, the main controller 71, the display unit 14, and the input unit 16. The measuring unit 30, the display unit 14, and the input unit 16 are connected to the main controller 71 so as to be able to transmit and receive signals to and from the main controller 71.

The measuring unit 30 is configured to include an optical surface plate 32, a light emitting unit 34, and a light receiving unit 36. In FIG. 11, elements of the measurement stick 50 other than the dielectric block 52 and the channel member 54 are not shown. Viewed from a lateral direction, a surface plate rail 32A constituted with an upper central horizontal surface, an emission inclined unit 32B inclined downward in a direction away from the surface plate rail 32A, and a reception inclined unit 32C arranged at the opposite side of the surface plate rail 32A to the emission inclined unit 32B, are formed on the optical surface plate 32. The measurement stick 50 is set on the surface plate rail 32A along the Y direction. The light emitting unit 34 emitting the irradiation lights L1 and L2 to the measurement stick 50 is arranged on the emission inclined unit 32B of the optical surface plate 32. Further, the light receiving unit 36 is arranged on the reception inclined unit 32C.

The light emitting unit 34 is configured to include a light source 34A and a lens unit 34B. The light receiving unit 36 is configured to include a lens unit 36A and a CCD 36B.

The light source 34A is connected to the control unit 70 for controlling the respective constituent elements of the biosensor 10 so as to be able to transmit and receive signals to and from the control unit 70. The light source 34A emits an irradiation light L in a divergent state. The irradiation light L emitted from the light source 34A is transmitted by the lens unit 34B and thereby split into the two irradiation lights L1 and L2. The irradiation lights L1 and L2 are incident on a pair of the measurement region E1 and the reference region E2 of the dielectric block 52 arranged on the optical surface plate 32, respectively.

The irradiation lights L1 and L2 are incident on the measurement region E1 and the reference region E2, respectively, at angles including various incident angle components with respect to the interface between the metal film 57 and the dielectric block 52 and equal to or greater than an angle of total reflection. Thus, a light source that can emit a light having angle spreading is provided as the light source 34A. Examples of the light source 34A include a laser, a superluminescent diode (SLD), an LED (light emitting diode), and a spectral filter.

In each of the irradiation lights L1 and L2 irradiated onto the metal film 57, a phenomenon occurs whereby reflected light attenuates for light at a specific incident angle included in each of the irradiation lights L1 and L2 (hereinafter, the phenomenon is often referred to as "reflected light attenuation"). This phenomenon results from the surface plasmon resonance (SPR) on the surface of the metal film 57.

SPR is a phenomenon defined as follows. When the irradiation light L is incident on the metal film 57, two waves are generated. That is, a low energy wave (a so-called evanescent wave) is generated on an emission-side surface of the metal film 57, and a compressional wave (a so-called evanescent wave) is generated on the interface between the dielectric block 52 and the metal film 57. When these evanescent waves are identical in wave number, i.e., match in wave number, these waves are in a resonant state. In the resonant state, at least a part of light energy transfers to the surface plasmon resonance, thereby causing a great reduction in the intensity of the light totally reflected by the interface between the metal film 57 and the dielectric block 52 (hereinafter, the reduction will be often referred to as "attenuated total reflection (ATR)"). That is, SPR is a phenomenon whereby the intensity of the light reflected from the metal film 57 undergoes attenuated total reflection. The evanescent waves are generated on an opposite surface of the metal film 57 to the surface on which the irradiation light L is incident when the irradiation light L is incident on the metal film 57 at a specific incident angle equal to or greater than the angle of total reflection.

A dielectric constant, which is expressed by a square of a refraction index, has an effect on the evanescent waves. Due to this, the interaction between the bioactive substance and the sample substance produced on the surface of the metal film 57 causes a difference in dielectric constant, the difference influences the surface plasmon resonance, and the influence can be understood as a change in resonance angle, that is, a change in refraction index.

When the interaction occurs between the bioactive substance and the sample substance contained in the supplied sample solution on the surface of the metal film 57, the dielectric constant of the surface of the metal film 57 changes and the refraction index (angle of resonance) changes. Thus, by selectively supplying different samples (sample solutions) to the bioactive substance on the surface of the metal film 57, it is possible to measure a change in refraction index at time series and to analyze the intermolecular interaction.

Specifically, each of the irradiation lights L1 and L2 totally reflected at the interface between the dielectric block 52 and the metal film 57 is received by the CCD 36B via the lens unit 36A. Because the incident lights L1 and L2 incident on the metal film 57 have angle spreading, the lights incident on the light receiving unit 36 likewise have angle spreading. The CCD 36B photoelectrically converts the received lights into electric signals as optical detection signals, and outputs the optical detection signals to the main controller 71.

The main controller 71 is configured to include a signal processor 38, the control unit 70, and a memory 17. The signal processor 38, the memory 17, the display unit 14, the input unit 16, the driving unit 49D, the first motor 27C, and the second motor 28C are connected to the control unit 70 so as to be able to transmit and receive signals to and from the control unit 70. The control unit 70 is constituted by a microcomputer including a CPU, a ROM, and a RAM. The memory 17 stores therein in advance various data as well as a processing routine shown in FIG. 12 to be described later in detail and the like.

The signal processor 38 obtains refraction index information on the measurement region E1 and the reference region E2 based on the optical detection signals input from the CCD 36B, and outputs the refraction index information to the control unit 70. During the measurement, the irradiation lights L1 and L2 are incident on the paired measurement region E1 and reference region E2 of the dielectric block 52, respectively. Thus, the optical detection signals from a plurality of regions, i.e., the measurement region E1 and the reference region E2 of the dielectric block 52 are input to the signal processor 38, and the refraction index information on the measurement region E1 and that on the reference region E2 are output to the control unit 70.

The signal processor 38 analyzes the respective input optical detection signals, thereby calculating an angle of attenuated total reflection $\theta sp$ as an incident angle at which the attenuated total reflection (ATR) occurs to each of the irradiation lights L1 and L2 in the measurement region E1 and the reference region E2 (i.e., an angle at which the intensity of the light totally reflected by the interface between the metal film 57 and the dielectric block 52 is greatly reduced).

By calculating the wave number of the SPR generated at the interface between the metal film 57 and the dielectric block 52 from the calculated angle of attenuated total reflection $\theta sp$, dielectric constants in the measurement region E1 and the reference region E2 are obtained. If the dielectric constants are obtained, refraction index information in the measurement region E1 and the reference region E2 are obtained because the dielectric constant is the square of the refraction index. Moreover, by correcting the refraction index information in the measurement region E1 with the reflection index information in the reference region E2, it is possible to obtain refraction index information of the sample substance in the measurement region E1.

When the refraction index information is output to the control unit 70, the control unit 70 can calculate the interaction (e.g., combined amount) between the sample substance in the sample solution and the bioactive substance based on the input refraction index information.

It is known that the refraction index of the organic solvent used as the solvent of the sample substance in the sample solution is so high as to influence accuracy for measuring the refraction index in the biosensor 10. Thus, if the concentration of the organic solvent in the sample solution supplied to the respective fluid channels 55 of the measurement stick 50 in the same measurement tip storage plate 48 has irregularities, it is feared that the accuracy for measuring the interaction between the bioactive substance and the sample substance may possibly be deteriorated.

To cope with the above situation, the biosensor 10 according to the embodiment adjusts the concentration of the organic solvent in the sample solution supplied into the respective fluid channels 55 of the measurement stick 50 to a predetermined concentration before measurement of the sample substance.

A method of adjusting the concentration of the organic solvent in the sample solution will now be described.

As stated, by irradiating the irradiation lights L1 and L2 from the light emitting unit 34 onto the measurement region E1 and the reference region E2 of one dielectric block 52, the optical detection signals are input to the signal processor 38 from the measurement region E1 and the reference region E2, respectively. For brevity of description, it is assumed that the optical detection signals are input only from one pair of the measurement region E1 and the reference region E2 among a plurality of measurement regions E1 and a plurality of reference regions E2 of one dielectric block 52.

Figure 12:
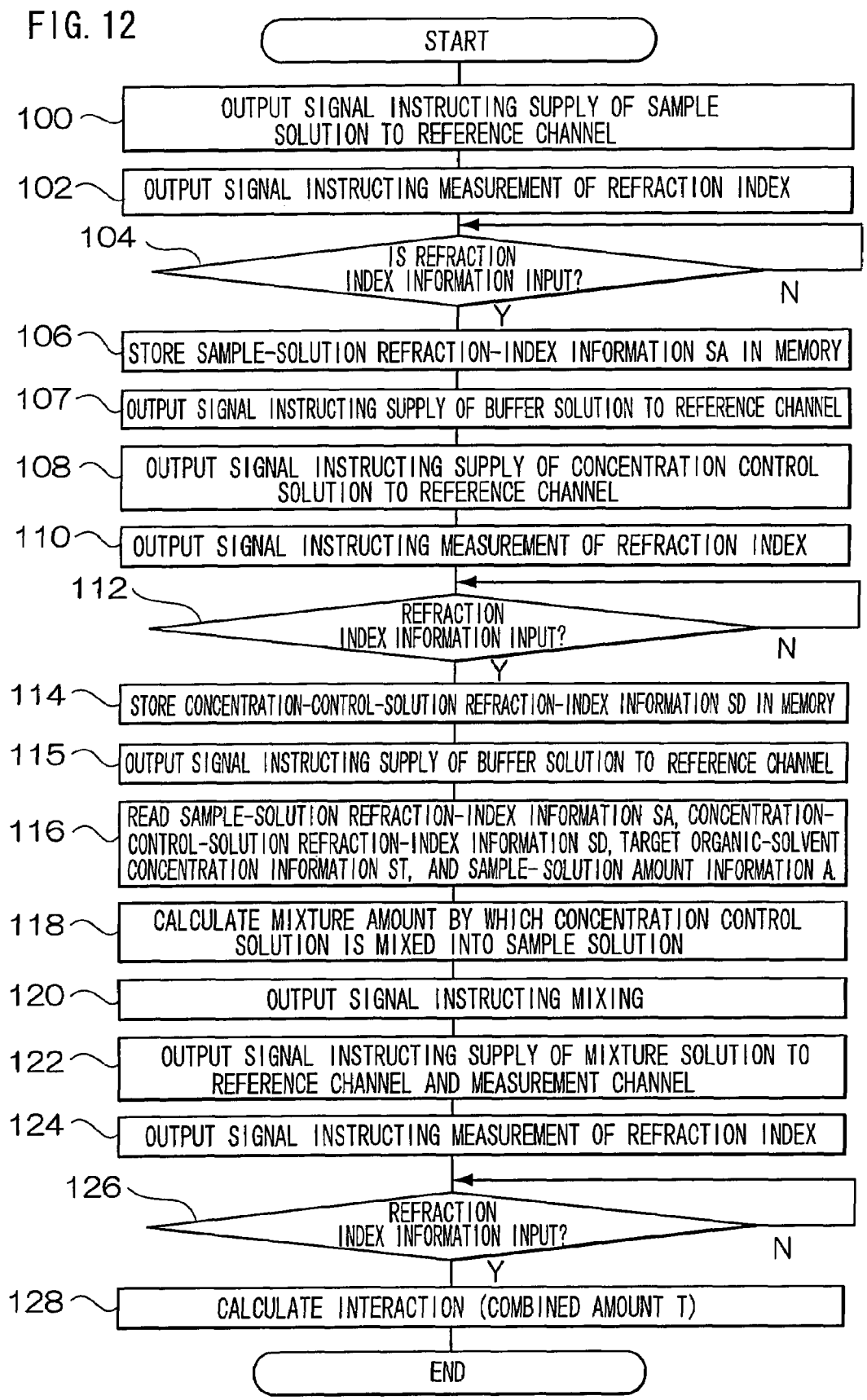
FIG. 12 is a flowchart showing processing performed by a controller.

When the input unit 16 is manipulated by the user, a signal instructing the biosensor 10 to start a measurement is input from the input unit 16, and subsequently, as a pre-process for the measurement, the control unit 70 executes the processing routine shown in FIG. 12 whenever one measurement stick 50 is set at the measuring unit 30.

The pre-process for the measurement is specifically as follows. The control unit 70 controls the driving unit 49D to move one measurement stick 50 from the measurement tip storage plate 48P to the measuring unit 30 by the measurement tip transport mechanism 49 and to set the measurement stick 50 at the measuring unit 30. Further, the control unit 70 controls the driving mechanism (not shown) to set one sample solution plate 40P at the sample solution setting unit 40B, and controls the driving mechanism (not shown) to set one concentration control solution plate 72P at the concentration control solution setting unit 72B. Moreover, the control unit 70 controls the driving mechanism (not shown) to set one pipette tip stocking unit 42P at the pipette tip setting unit 42B, and controls the driving mechanism (not shown) to set one mixing plate 74P at the mixing plate setting unit 74B.

At step 100, a signal that instructs supply of a sample solution (hereinafter, referred to as "sample solution supply instruction signal") is output to the motor 22B, the motor 24A, the first motor 27C, and the second motor 28C. This sample solution supply instruction signal includes an instruction signal instructing supply of the sample solution in one of the cells of the sample solution plate 40P to the reference channel 55R of the measurement stick 50 set at the measuring unit 30 and a supply amount signal indicating a supply amount of the sample solution.

The supply amount of the sample solution at step 100 suffices to exceed an amount by which the reference channel 55R is filled with the sample solution. The supply amount of the sample solution may be stored in the memory 17 in advance and read from the memory 17.

Figure 13:
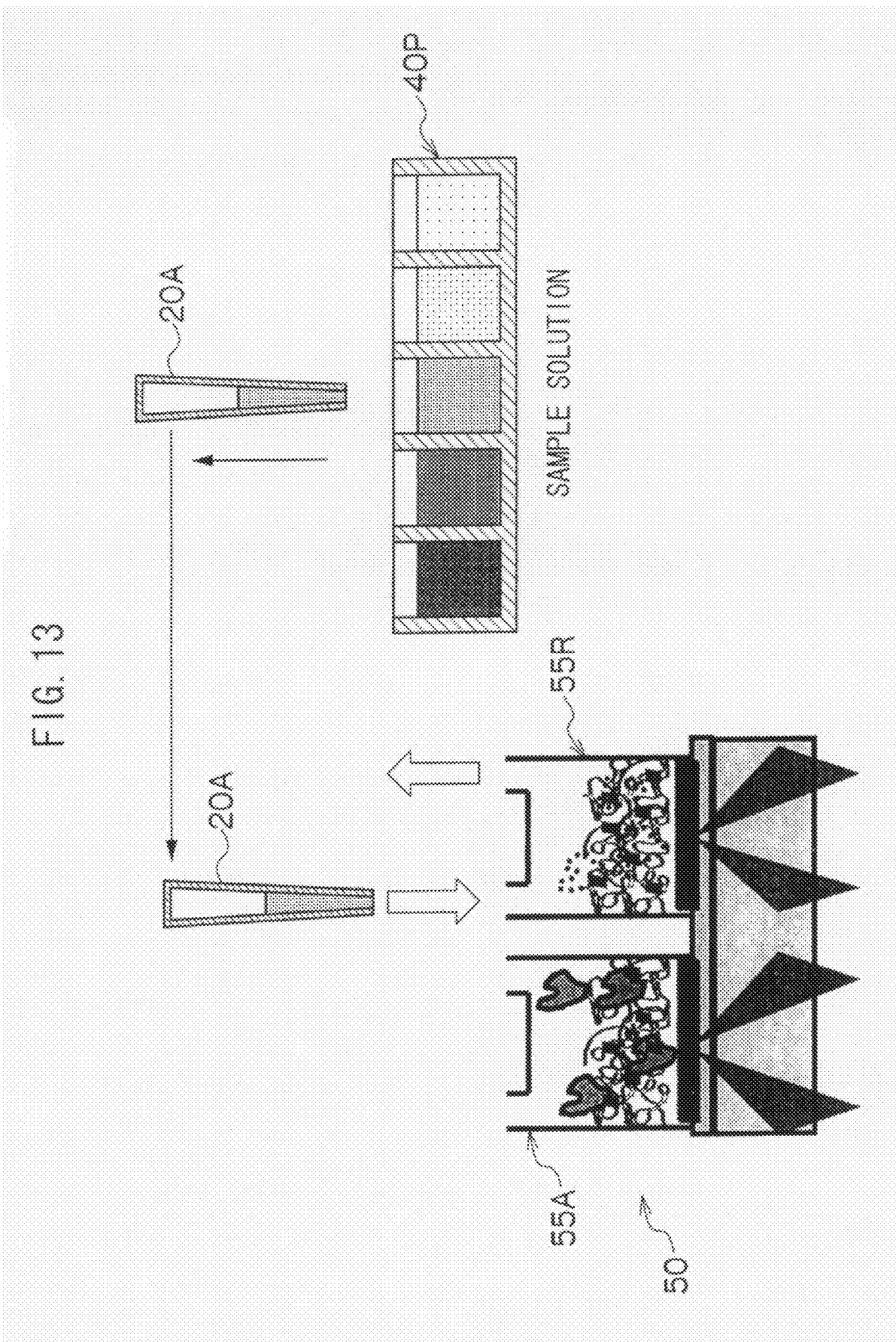
FIG. 13 is a pattern diagram showing a step of supplying a sample solution extracted from a sample solution plate to the reference region (reference channel) according to an embodiment of the invention.

When the sample solution supply instruction signal is input, the motors 24A and 22B for driving the dispensing head 20 in the X and Z directions are driven and the first motor 27C and the second motor 28C for adjusting absorption/discharge of the dispensing tubes 20A of the dispensing head 20 are driven. As a result, as shown in FIG. 13, the sample solution is supplied to the reference channel 55R of the measurement stick 50 set to the measuring unit 30.

At step 102, a measurement instruction signal is output to the light source 34A. When the measurement instruction signal is input to the light source 34A, the light source 34A emits the irradiation light L to the reference region E2 and the measurement region E1.

At step 104, a negative determination is repeated until refraction index information is input from the signal processor 38, and when a positive determination is made, the input refraction index information is in the memory 17 as sample-solution refraction-index information Sa indicating the refraction index of the sample solution at step 106. In the processing at step 104, only the sample-solution refraction-index information Sa from the reference region E2 in the reference channel 55R is stored in the memory 17. This is because the sample solution is supplied only to the reference channel 55R out of the measurement channel 55A and the reference cannel 55R and not to the measurement channel 55A in the processing at step 100.

At step 107, a signal instructing supply of the buffer solution (hereinafter, "buffer solution supply instruction signal") is output to the motor 22B, the motor 24A, the first motor 27C, and the second motor 28C. This buffer solution supply instruction signal includes an instruction signal instructing supply of the buffer solution in the buffer solution plate 44P to the reference channel 55R of the measurement stick 50 set to the measuring unit 30 and a supply amount signal indicating a supply amount of the buffer solution.

The supply amount of the buffer solution at the step 107 suffices to exceed an amount by which the reference channel 55R is filled with the buffer solution. The supply amount of the buffer solution may be stored in the memory 17 in advance and read from the memory 17.

When the buffer solution supply instruction signal is input, the motors 24A and 22B for driving the dispensing head 20 in the X and Z directions are driven and the first motor 27C and the second motor 28C for adjusting absorption/discharge of the dispensing tubes 20A of the dispensing head 20 are driven. As a result, the buffer solution is supplied to the reference channel 55R of the measurement stick 50 set to the measuring unit 30. In addition, the sample solution supplied to the reference channel 55R by the processing at the step 100 is removed from the reference channel 55R.

At step 108, a signal instructing supply of the concentration control solution (hereinafter, "concentration control solution supply instruction signal") is output to the motor 22B, the motor 24A, the first motor 27C, and the second motor 28C. This concentration control solution supply instruction signal includes an instruction signal instructing supply of the concentration control solution in one of the cells of the concentration control solution plate 72P to the reference channel 55R of the measurement stick 50 set at the measuring unit 30 and a supply amount signal indicating a supply amount of the concentration control solution.

The supply amount of the concentration control solution at step 108 suffices to exceed an amount by which the reference channel 55R is filled with the concentration control solution. The supply amount of the concentration control solution may be stored in the memory 17 in advance and read from the memory 17.

Figure 14:
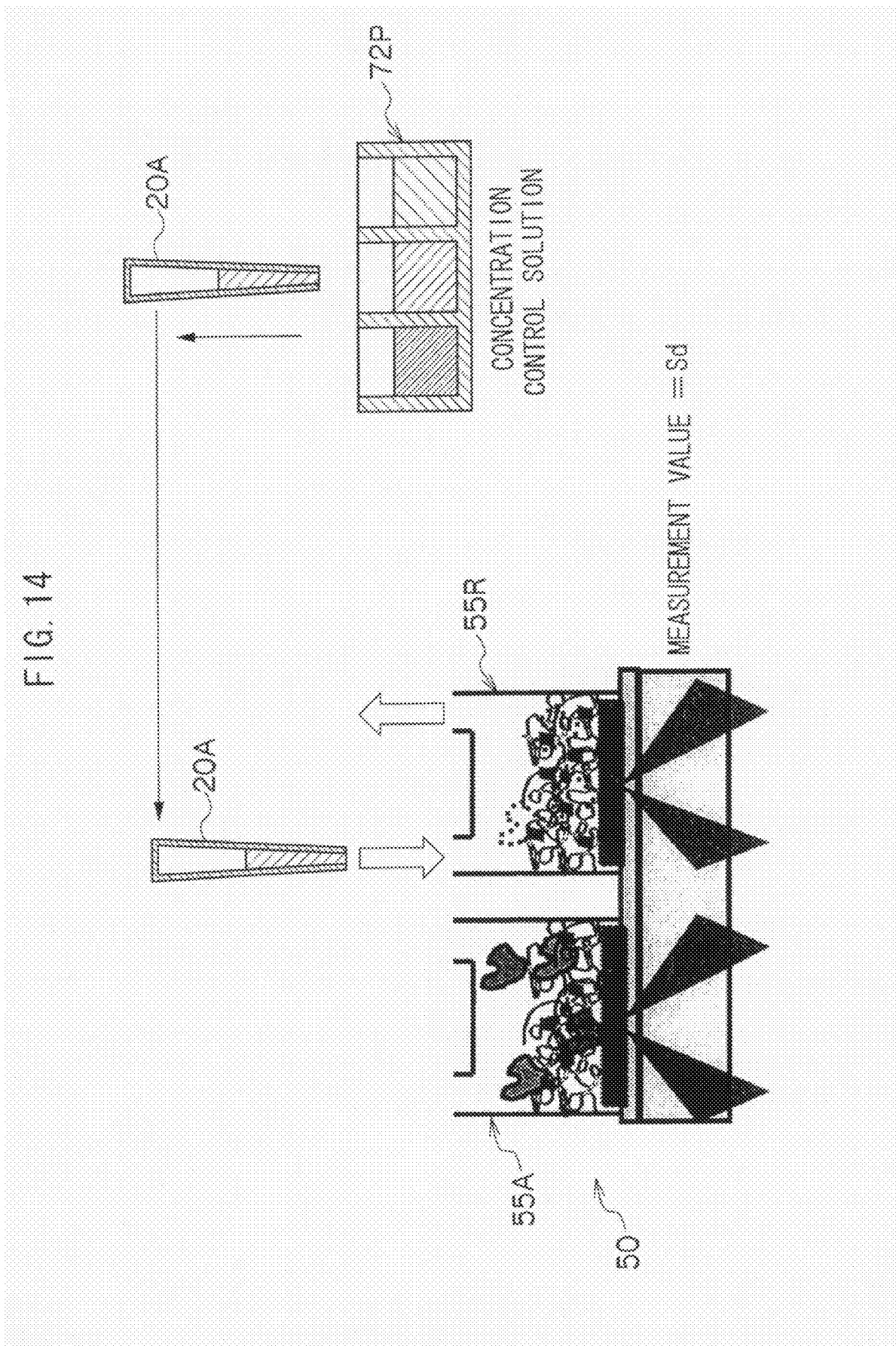
FIG. 14 is a pattern diagram showing a step of supplying a concentration control solution extracted from a concentration control solution plate to the reference region (reference channel) according to an embodiment of the invention.

When the concentration control solution supply instruction signal is input, the motors 24A and 22B for driving the dispensing head 20 in the X and Z directions are driven and the first motor 27C and the second motor 28C for adjusting absorption/discharge of the dispensing tubes 20A of the dispensing head 20 are driven. As a result, as shown in FIG. 14, the concentration control solution is supplied to the reference channel 55R of the measurement stick 50 set to the measuring unit 30.

At step 110, a measurement instruction signal is output to the light source 34A. When the measurement instruction signal is input to the light source 34A, the light source 34A emits irradiation light L to the reference region E2 and the measurement region E1.

At step 112, a negative determination is repeated until refraction index information is input from the signal processor 38, and when a positive determination is made, the input refraction index information is stored in the memory 17 as concentration-control-solution refraction-index information Sd indicating the refraction index of the concentration control solution at step 114. In the processing at step 112, only the concentration-control-solution refraction-index information Sd from the reference region E2 in the reference channel 55R is stored in the memory 17. This is because the concentration control solution is supplied only to the reference channel 55R out of the measurement channel 55A and the reference cannel 55R and not to the measurement channel 55A in the processing at the step 108.

At step 115, similarly to step 107, a buffer solution supply instruction signal is output to the motor 22B, the motor 24A, the first motor 27C, and the second motor 28C. This buffer solution supply instruction signal includes an instruction signal instructing supply of the buffer solution in the buffer solution plate 44P to the reference channel 55R of the measurement stick 50 set to the measuring unit 30 and a supply amount signal indicating a supply amount of the buffer solution.

When the buffer solution supply instruction signal is input, the motors 24A and 22B for driving the dispensing head 20 in the X and Z directions are driven and the first motor 27C and the second motor 28C for adjusting absorption/discharge of the dispensing tubes 20A of the dispensing head 20 are driven. As a result, the buffer solution is supplied to the reference channel 55R of the measurement stick 50 set to the measuring unit 30. In addition, the concentration control solution supplied to the reference channel 55R by the processing at the step 108 is removed from the reference channel 55R.

At step 116, the sample-solution refraction-index information Sa indicating the refraction index of the sample solution stored in the memory 17 at step 106, the concentration-control-solution refraction-index information Sd indicating the refraction index of the concentration control solution stored in the memory 17 at step 114, target organic-solvent concentration information St, and sample-solution amount information A are read from the memory 17.

The target concentration information refers to information indicating a target concentration that is preset as the concentration of the organic solvent in the measurement target sample solution during the measurement of the interaction between the sample substance and the bioactive substance by the biosensor 10.

The target concentration may be set in advance for every measurement target sample substance or for every measurement tip storage plate 48P. Alternatively, one target concentration may be set in advance as concentrations of the organic solvent in all the sample solutions to be measured by the biosensor 10 in advance. The preset target concentration information may be stored in the memory 17 in advance.

The sample-solution amount information refers to information indicating an amount of the sample solution used during a mixing processing for mixing the concentration control solution into the sample solution to be described later and which is stored in the memory 17 in advance. The sample solution amount represented by the sample-solution amount information may be an amount with which, for example, both the reference channel 55R and the measurement channel 55A are filled with the sample solution. In the present embodiment, it is assumed that information indicating A µL is set as the amount of the sample solution in advance.

At step 118, a mixture amount of the concentration control solution to be mixed into the sample solution is calculated so that the concentration of the organic solvent in the sample solution supplied to the reference channel 55R by the processing at the step 100 becomes equal to the target concentration read at step 116.

In the processing at the step 118, a mixture amount D µL by which the concentration control solution is mixed into the sample solution is calculated based on the sample-solution refraction-index information Sa indicating the refraction index of the sample solution, the concentration-control-solution refraction-index information Sd indicating the refraction index of the concentration control solution, the target organic-solvent concentration information St, and the sample-solution amount information A µL read at the step 116.

$$(Sa \times A)+(Sd \times D)=St \times (A+D) \tag{1}$$

In the processing at step 118, the mixture amount D µL by which the organic solvent is added to the sample solution is calculated so that the concentration of the organic solvent in the sample solution the refraction index of which is measured at the step 116 is equal to the target organic solvent concentration of the target organic-solvent concentration information St.

At step 120, a mixture instruction signal instructing mixing of the sample solution supplied to the reference channel 55R at the step 100 with the concentration control solution supplied to the reference channel 55R at the step 108 is output to the motor 22B, the motor 24B, the first motor 27C, and the second motor 28C.

This mixture instruction signal includes an instruction signal instructing mixing of the sample solution with the concentration control solution, the sample solution amount information A µL read at the step 116, and the mixture amount information D µL calculated at the step 118.

When the mixture instruction signal is input, the motors 24A and 22B for driving the dispensing head 20 in the X and Z directions are driven and the first motor 27C and the second motor 28C for adjusting absorption/discharge of the dispensing tubes 20A of the dispensing head 20 are driven. As a result, the sample solution supplied to the reference region E2 from one of the cells of the sample solution plate 40P at the step 100 is supplied to a predetermined cell of the mixing plate 74P (i.e., a cell corresponding to the measurement target measurement channel 55A) by the amount A µL. In addition, the concentration control solution supplied to the reference region E2 from one of the cells of the concentration control solution plate 72P at the step 108 is supplied to the predetermined cell of the mixing plate 74P by D µL (see FIG. 15).

In the processing at the step 120, the mixture solution in which the concentration control solution supplied to the sample region E2 at the step 108 is mixed into the sample solution supplied by A µL to the reference region E2 at the step 100 by the mixture amount D µL calculated at the step 118 is prepared.

At step 122, a signal that instructs supply of the mixture solution (hereinafter, referred to as "mixture solution supply instruction signal") is output to the motor 22B, the motor 24A, the first motor 27C, and the second motor 28C. This mixture solution supply instruction signal includes an instruction signal instructing supply of the mixture solution in one of the cells of the mixture solution plate 74P prepared at step 120 to the reference channel 55R and the measurement channel 55A of the measurement stick 50 set to the measuring unit 30, and a supply amount signal indicating a supply amount of the mixture solution. The supply amount of the mixture solution suffices to exceed the amount with which the reference channel 55R and the measurement channel 55A are filled with the mixture solution. The supply amount of the mixture solution may be stored in the memory 17 in advance and read from the memory 17.

When the mixture solution supply instruction signal is input, the motors 24A and 22B for driving the dispensing head 20 in the X and Z directions are driven and the first motor 27C and the second motor 28C for adjusting absorption/discharge of the dispensing tubes 20A of the dispensing head 20 are driven. As a result, as shown in FIG. 16, the sample solution is supplied to each of the reference channel 55R and the measurement channel 55A of the measurement stick 50 set at the measuring unit 30 (see FIG. 16).

At step 124, a measurement instruction signal is output to the light source 34A. When the measurement instruction signal is input to the light source 34A, the light source 34A emits the irradiation light L to the reference region E2 and the measurement region E1.

At step 126, a negative determination is repeated until the refraction index information is input from the signal processor 38, and when a positive determination is made, a combined amount T of the bioactive substance and the sample substance is calculated as the interaction between the bioactive substance and the sample substance in the mixture solution based on the refraction index information of the reference region E2 and that of the measurement region E1 input at the step 126. Thereafter, the processing routine shown in FIG. 12 is finished.

It is to be noted that the processes from step 100 to step 104 correspond to functions of a first measuring unit of a measuring apparatus according to the invention, and the processes from step 108 to step 112 correspond to functions of a second measuring unit of the measuring apparatus according to the invention. Furthermore, the processing at the step 118 corresponds to a function of a calculating unit of the measuring apparatus according to the invention. The process at step 122 corresponds to a function of a supply unit of the measuring apparatus according to the invention. The processes from step 122 to step 128 correspond to functions of a third measuring unit of the measuring apparatus according to the invention.

As discussed above, the biosensor 10 according to the present embodiment mixes the concentration control solution into the sample solution so that the concentration of the organic solvent in the measurement target sample solution is equal to a preset concentration, and measures the interaction between the sample substance and the bioactive substance in the mixture solution, thereby making it possible to suppress a decrease in measurement accuracy due to irregularity in the concentration of the organic solvent.

Furthermore, for the control of the concentration of the organic solvent in the measurement target sample solution, a measuring mechanism (the light emitting unit 34, the light receiving unit 36, the measurement stick 50, the measuring unit 30, and the dispensing head 20) for measuring the interaction between the sample substance in the sample solution and the bioactive substance is used to measure the refraction index of the measurement target sample solution, thereby measuring the concentration of the organic solvent in the sample solution. Furthermore, the measuring mechanism is used to measure the refraction index of the concentration control solution mixed into the sample solution, thereby measuring the concentration of the organic solvent in the concentration control solution. Thus, it is possible to control the concentration of the organic solvent in the sample solution with a simplified structure.

In the above-described embodiment, for the brevity of description, it is assumed that the optical detection signals are input only from one pair of the measurement region E1 and the reference region E2 among a plurality of measurement regions E1 and a plurality of reference regions E2 of one dielectric block 52. Alternatively, the optical detection signals may be input from the respective pairs of the measurement regions E1 and the reference regions E2 of one dielectric block 52. In this case, the control unit 70 may control the concentration of the organic solvent in the sample solution by performing the processings from the step 100 to the step 122 for each of a plurality of fluid channels 55 of the dielectric block 52, and obtain the interaction between the sample substance and the bioactive substance by performing the processings from the step 122 to the step 128 based on the result of causing the signal processor 38 to obtain refraction index information on a plurality of measurement regions E1 and a plurality of reference regions E2 from the input optical detection signals input.

Moreover, according to the present embodiment, description has been given of the instance in which the measuring apparatus measures the interaction between the bioactive substance and the sample substance by measuring a change in angle of resonance caused by the surface plasmon resonance. However, any other biosensor based on, for example, a quartz crystal microbalance (QCM) measuring technique or an optical measuring technique using a functionalized surface from colloidal particles to superfine particles of gold is applicable to the measuring apparatus of the invention.

Furthermore, the prism unit 52A of the biosensor 10 may be replaced by a diffraction grating as the spectral unit. In this alternative, the signal processor 38 performs a waveform analysis for measuring a change in the refraction index of the irradiation light L emitted from the light emitting unit 34 in the measurement region E1 and the reference region E2 as a waveform change. It is thereby possible to apply the invention to the measurement of the interaction between the bioactive substance and the sample substance.

According to the measuring apparatus and the measuring method of the invention, the interaction between the bioactive substance and the sample substance is measured for the mixture solution in which the concentration control solution is mixed into the sample solution so that the concentration of the organic solvent in the measurement target sample solution is equal to the preset concentration. It is, therefore, possible to provide the measuring apparatus and the measuring method capable of suppressing deterioration in measurement accuracy during measurement of the interaction between the bioactive substance and the sample substance.

While the present invention has been illustrated and described with respect to specific exemplary embodiments thereof, it is to be understood that the present invention is by no means limited thereto and encompasses all changes and modifications which will become possible without departing from the spirit and scope of the present invention.

What is claimed is:

1. A measuring apparatus comprising:
   a first measuring unit that measures a concentration of an organic solvent in a sample solution obtained by dissolving a sample substance as a measurement target in the organic solvent;
   a second measuring unit that measures a concentration of the organic solvent in a concentration control solution which does not contain the sample substance but contains the organic solvent;
   a calculating unit that calculates a mixture amount of the concentration control solution to be mixed into a preset amount of the sample solution so that the concentration of the organic solvent in the sample solution is equal to a preset concentration based on the concentration measured by the first measuring unit and the concentration measured by the second measuring unit;
   a mixing unit that mixes the mixture amount of the concentration control solution calculated by the calculating unit with the preset amount of the sample solution; and
   a third measuring unit that supplies a mixture solution obtained by the mixing unit to a measurement region in which a bioactive substance is immobilized in advance, and measuring an interaction between the bioactive substance and the sample substance in the mixture solution based on a result of measuring a refraction index of a light incident on the measurement region.

2. The measuring apparatus according to claim 1, wherein:
the first measuring unit measures a refraction index of the sample solution as the concentration of the organic solvent in the sample solution; and
the second measuring unit measures a refraction index of the concentration control solution as the concentration of the organic solvent in the concentration control solution.

3. The measuring apparatus according to claim 2, wherein:
the first measuring unit supplies the sample solution to a reference region in which the bioactive substance is not immobilized, and measures a refraction index of a light incident on the reference region as the concentration of the organic solvent in the sample solution; and
the second measuring unit supplies the concentration control solution to the reference region, and measures the refraction index of the light incident on the reference region as the concentration of the organic solvent in the concentration control solution.

4. The measuring apparatus according to claim 3, wherein the third measuring unit measures an angle of resonance caused by a surface plasmon resonance in the measurement region as the refraction index of the light.

5. The measuring apparatus according to claim 3, wherein the third measuring unit includes a spectral unit that disperses a reflected light in the measurement region to emit the dispersed reflected light, and measures a wavelength of resonance caused by a surface plasmon resonance in the measurement region as the refraction index of the light.

6. The measuring apparatus according to claim 2, wherein the third measuring unit includes a spectral unit that disperses a reflected light in the measurement region to emit the dispersed reflected light, and measures a wavelength of resonance caused by a surface plasmon resonance in the measurement region as the refraction index of the light.

7. The measuring apparatus according to claim 1, wherein the third measuring unit measures an angle of resonance caused by a surface plasmon resonance in the measurement region as the refraction index of the light.

8. The measuring apparatus according to claim 2, wherein the third measuring unit measures an angle of resonance caused by a surface plasmon resonance in the measurement region as the refraction index of the light.

9. The measuring apparatus according to claim 7, wherein the third measuring unit includes a spectral unit for dispersing a reflected light in the measurement region to emit the dispersed reflected light, and measures a wavelength of resonance caused by a surface plasmon resonance in the measurement region as the refraction index of the light.

10. The measuring apparatus according to claim 1, wherein the third measuring unit includes a spectral unit that disperses a reflected light in the measurement region to emit the dispersed reflected light, and measures a wavelength of resonance caused by a surface plasmon resonance in the measurement region as the refraction index of the light.

11. A measuring method comprising:
a first measuring process of measuring a concentration of an organic solvent in a sample solution obtained by dissolving a sample substance as a measurement target in the organic solvent;
a second measuring process of measuring a concentration of the organic solvent in a concentration control solution which does not contain the sample substance but contains the organic solvent;
calculating a mixture amount of the concentration control solution to be mixed into a preset amount of the sample solution so that the concentration of the organic solvent in the sample solution becomes equal to a preset concentration based on the concentration measured by the first measuring process and the concentration measured by the second measuring process;
mixing the mixture amount of the concentration control solution calculated in the calculating with the preset amount of the sample solution; and
a third measuring process of supplying a mixture solution obtained by the mixing to a measurement region in which a bioactive substance is immobilized in advance, performing an analysis using a refraction index of a light incident on the measurement region, and measuring an interaction between the bioactive substance and the sample substance in the mixture solution.

12. The measuring method according to claim 11, wherein:
in the first measuring process, a refraction index of the sample solution is measured as the concentration of the organic solvent in the sample solution; and
in the second measuring process, a refraction index of the concentration control solution is measured as the concentration of the organic solvent in the concentration control solution.

* * * * *